(12) United States Patent
Zalipsky et al.

(10) Patent No.: US 6,586,002 B2
(45) Date of Patent: *Jul. 1, 2003

(54) ENHANCED CIRCULATION EFFECTOR COMPOSITION AND METHOD

(75) Inventors: Samuel Zalipsky, Redwood City, CA (US); Martin C. Woodle, Menlo Park, CA (US); Francis J. Martin, San Francisco, CA (US); Yechezkel Barenholz, Jerusalem (IL); Herve Bercovier, Jerusalem (IL)

(73) Assignee: Alza Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/877,978

(22) Filed: Jun. 8, 2001

(65) Prior Publication Data

US 2001/0043929 A1 Nov. 22, 2001

Related U.S. Application Data

(63) Continuation of application No. 08/480,332, filed on Jun. 7, 1995, now Pat. No. 6,180,134, which is a continuation-in-part of application No. 08/316,436, filed on Sep. 29, 1994, now abandoned, which is a continuation-in-part of application No. 08/035,443, filed on Mar. 23, 1993, now Pat. No. 6,326,353.

(51) Int. Cl.$^7$ .............................................. A61K 9/127
(52) U.S. Cl. ...................... 424/450; 424/812; 424/85.2; 424/85.4; 424/85.8; 530/319; 530/391.1; 530/350; 530/324; 530/325; 530/326; 530/327; 530/328; 530/329; 530/330; 530/331
(58) Field of Search ................................ 424/450, 85.8, 424/85.2, 85.4, 812; 530/319, 391.1, 350, 331–324

(56) References Cited

U.S. PATENT DOCUMENTS

| | | | |
|---|---|---|---|
| 4,179,337 A | 12/1979 | Davis et al. | |
| 4,948,590 A | 8/1990 | Hawrot et al. | |
| 5,013,556 A | 5/1991 | Woodle et al. | |
| 5,092,885 A | 3/1992 | Yamada et al. | |
| 5,527,528 A | 6/1996 | Allen et al. | |
| 6,180,134 B1 | * 1/2001 | Zalipsky et al. | |

FOREIGN PATENT DOCUMENTS

| | | |
|---|---|---|
| EP | 339 504 A2 | 11/1989 |
| EP | 428 486 A1 | 5/1991 |
| WO | WO 90/14103 | 11/1990 |

OTHER PUBLICATIONS

Blume, G., et al., "Specific targeting with poly(ethylene glycol)–modified liposomes: coupling of homing devices to the ends of the polymeric chains combines effective target binding with long circulation times," *Biochimica et Biophysica Acta*, 1149:180–184 (1993).

Cross, A.S., et al., "Choice of bacteria in animal models of sepsis," *Infect Immun.*, 61(7):2741–2747 (1993).

deAzavedo, J.C.S., et al., "Bacterial Endotoxins: Structure, Biomedical Significance and Detection with the Limulus Amebocyte Lysate Test" pp. 419–430 (1985).

Endo, S., et al., "Treatment of endotoxemia with low–dose intramuscular injections or oral administration of polymyxin B," *Clinical Therapeutics*, 14(1):64–67 (1992).

Feist, W., et al., "Modulation of lipopolysaccharide–induced production of tumor necrosis factor, interleukin 1, and interleukin 6 by synthetic precursor Ia of lipid A," *FEMS Microbiology Immunology* 89:73–90 (1992).

Fitzer–SchillerReuter, G., "Centocor Stops Trials of Flagship Drug," Washington Post Finacial Section, Jan. 19, 1993, pp. d3.

Harris, W.J. and Emery, S., "Therapeutic antibodies–the coming of age," *Trends Biotechnol*, 11(2):42–44 (1993).

Hird, *Genes & Cancer*, pp. 183–189 (1990).

Hunefeld, G., "A clinical study of selective gut decolonization in 204 long–term ventilated intensive care patients undergoing abdominal and accident surgery," *Anaesthesiol. Reanimat.*, 14(3):131–153 (1989).

Iwamoto, Y., et al., "YIGSR, a Synthetic Laminin Pentapeptide, Inhibits Experimental Metastasis Formation," *Science* 238:1132–1134 (1987).

Kawasaki, K., et al., "Amino Acids and Peptides. XIV. Laminin Related Peptides and Their Inhibitory Effect On Experimental Metastasis Formation," *Biochemical and Biophysical Research Communications*, 174(3):1159–1162 (1991).

Klibanov, A.L., and L. Huang, "Long–Circulating Liposomes: Development and Perspectives," *Journal of Liposome Research*, 2(3):321–334 (1992).

Manson, W.L., et al., "Selective intestinal decontamination for prevention of wound colonization in severely burned patients: a retrospective analysis," *Burns*, 18(2):98–102 (1992).

Munster, A., et al., "Control of endotoxemia in burn patients by use of polymyxin B," *J. Burn Care Rehabil.*, 10(4):327–330 (1989).

Murata, J., et al., "Inhibitory effect of a synthetic polypeptide, poly(Tyr–Ile–Gly–Ser–Arg), on the metastatic formation of malignant tumour cells," *Int. J. Biol. Macromol.*, 11:97–99 (1989).

Osband, M.E. and Ross, S., "Problems in the investigational study and clinical use of cancer immunotherapy," *Immunol Today.*, 11(6):193–195 (1990).

(List continued on next page.)

Primary Examiner—Sheela Huff
(74) Attorney, Agent, or Firm—Perkins Coie LLP

(57) ABSTRACT

A liposome composition comprising small, surface-bound effector molecules is disclosed. The liposomes have a surface layer of hydrophilic polymer chains, for enhanced circulation time in the bloodstream. The effector molecules are attached to the distal ends of the polymer chains. In one embodiment, the effector is polymyxin B, for treatment of septic shock.

48 Claims, 13 Drawing Sheets

OTHER PUBLICATIONS

Saiki, I., et al., "Antimetastatic effects of synthetic polypeptides containing repeated structures of the cell adhesive Arg–Gly–Asp (RGD) and Tyr–Ile–Gly–Ser–Arg (YIGSR) sequences," *Br. J. Cancer*, 60: 722–728 (1989).

Sastry, P.A., et al., "Comparative Studies of the Amino Acid and Nucleotide Sequences of Pilin Derived from *Pseudomonas aeruginosa* PAK and PAO," *Journal of Bacteriology* 164(2):571–577 (1985).

* cited by examiner

I

TEA

TEA

TEA, DSPE

ACIDOLYSIS

To Fig 1 con't

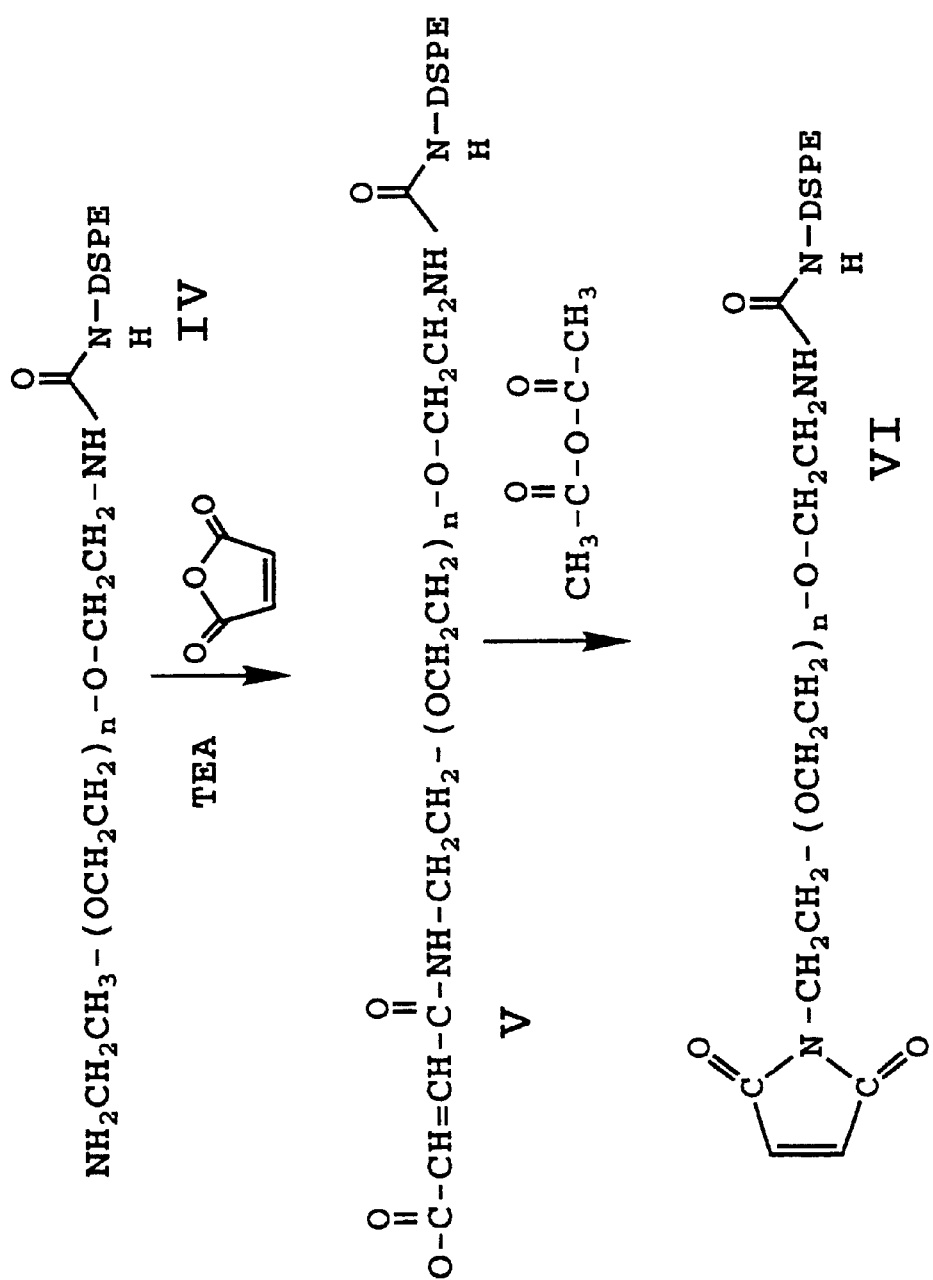
Fig. 1 con't

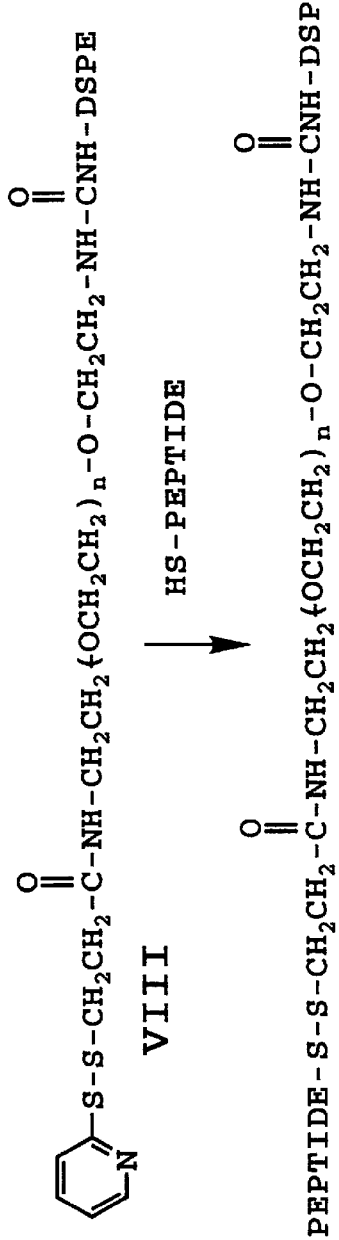
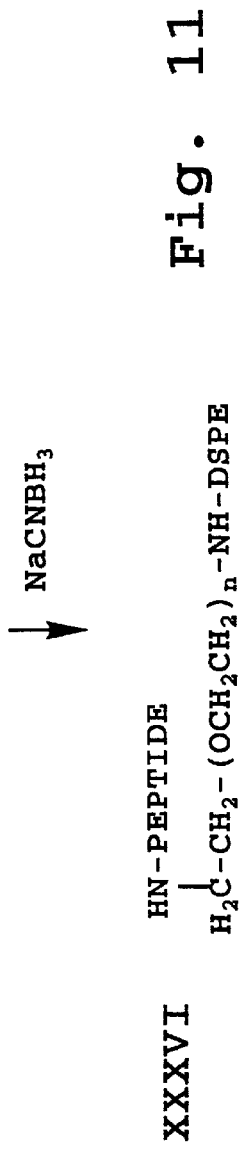
Fig. 10
Fig. 11

ENHANCED CIRCULATION EFFECTOR COMPOSITION AND METHOD

This application is a continuation of U.S. application Ser. No. 08/480,332 filed Jun. 7, 1995, now U.S. Pat. No. 6,180,134; which is a continuation-in-part of U.S. application Ser. No. 08/316,436 filed Sep. 29, 1994, now abandoned; which is a continuation-in-part of U.S. application Ser. No. 08/035,443 filed Mar. 23, 1993, now U.S. Pat. No. 6,326,353; all of which are incorporated herein in its entirety by reference.

1. FIELD OF THE INVENTION

The present invention relates to an enhanced-circulation effector composition and method for treating a subject with small effector molecules which are normally subject to rapid renal clearance from the bloodstream.

2. REFERENCES

Abbas, A. K., et al., (1991) In: Cellular and Molecular Immunology, W. B. Saunders Company Harcourt Brace Jovanovich, Philadelphia.
Abuchowski, A., et al., (1984) Cancer Biochem. Biophys. 7:175–186.
Baldwin, G., et al., (1991) J. Infect. Diseas. 164:542–549.
Borman, S. (1992) Chem. Eng. News, December 7: 25–28.
Capon, D. J. and Ward, R. H. R. (1991) Ann. Rev. Immunol. 9:649–678.
Chen, L. L., et al., (1991) J. Biol. Chem. 266:18237–18243.
Cherng, W.-J., et al., (1992) Amer. Heart J. 123(4):841–845.
Dinarello, C. A. (1991) Blood 77(8):1627–1650.
Grines, C. L., et al., (1991) Circulation 84(2):540–549.
Harlow, E., et al., Antibodies: A Laboratory Manual, Cold Spring Harbor, 1988.
Harris, J. M. (1984) J. Polym. Sci., Polym. Chem. Ed. 22:341–352.
Hershfield, M. S., et al., (1982) New Engl. J. Med. 316(10):589–595.
Ichikawa, Y. et al., (1992) J. Am. Chem. Soc. 114:9283–9298.
Inman, J. K. (1974) Meth. Enzymol. 34:30–58.
Janeway, C. A. (1992) Ann. Rev. Immunol. 10:645–674.
Jawetz, E. (1987) In: Basic and Clinical Pharmacology (Katzung, B. G., ed.) Apple & Lange, Los Altos, Calif., pg. 511.
Kano, J., et al., (1991) Biochem. Biophys. Res. Comm. 179:97–101.
Katre, N. V., et al., (1987) Proc. Natl. Acad. Sci. USA 84:1487–1491.
Larrick, J. W., et al., Methods in Immunology 2: 106 (1991).
Maniatis, T., et al. (1989) In: Molecular Cloning: A Laboratory Manual, Cold Spring Harbor Laboratory Press.
Martin, F. J. (1990) In: Specialized Drug Delivery Systems-Manufacturing and Production Technology, (P. Tyle, ed.) Marcel Dekker, New York, pp. 267–316.
Myers, M. L., et al., (1985) Lab. Investig. 72(4):915–920.
Philips, M. L., et al., (1990) Science 250:1130–1132.
Salomom, S. E. (1987) In: Basic and Clinical Pharmacology (Katzung, B. G., ed.) Apple & Lange, Los Altos, Calif., pg. 713.
Stylianou, E., et al.,(1992) J. Biol. Chem. 267:15836–15841.
Szoka, F., Jr., et al. (1978) Proc. Natl. Acad. Sci. USA 75:4194.
Szoka, F., Jr., et al. (1980) Ann. Rev. Biophys. Bioeng. 9:467.
Wainright, N. R., et al. (1990) In: Cellular and Molecular Aspects of Endotoxin Reactions (eds. Nowotny. A et al.) Elsevier Science Publishers B. V. p. 315.
Waldmann, T. A. (1992) Annu. Rev. Immunol. 10:675–704.
Wilchek, M., and Bayer, E. A. (1987) Meth. Enzymol. 138:429–442.
Zalipsky, S., et al., (1986) Polymer Preprints 27(1):1.
Zalipsky, S., et al., (1987) Int. J. Peptide Res. 30:740.
Zalipsky, S., et al., (1990) J. Bioactive Compat. Polym. 5:227.
Zaplipsky, S., et al., (1991) *Polymeric Drugs* (Dunn, R. L. and Ottenbrete, R. M., eds.) American Chemical Society, pp. 91.
Zalipsky, S., et al., (1992a) *Poly (Ethylene Glycol) Chemistry: Biotechnical and Biomedical Applications* (J. M. Harris, ed.) Plenum Press, pg. 347–370.
Zalipsky, S., et al., (1992b) Biotechnol. Appl. Biochem. 15:100.
Zheng, B., et al., (1992) Science 256:1560–1563.

3. BACKGROUND OF THE INVENTION

A number of emerging or current therapies involve intravenous injection of small (less than 50 Kdaltons) protein, polypeptide or polysaccharide effectors. Such effectors can include $F_{ab}$ antibody fragments, for use in active immunity; cytokines and cellular growth factors, for stimulating immunological inflammatory responses; hormones; and polysaccharides, which are capable of interacting with endothelial cell receptors to competitively block neutrophil binding to activated endothelial cells lining the blood vessel (Katre, Philips, Waldmann).

Other small polypeptide effectors have been proposed for use in blocking viral infection of target cells in the blood, such as a CD4+ glycopeptide which is effective to inhibit binding of human immunodeficiency virus (HIV) to $CD4^+$ cells (Capon, Janeway).

Polymyxin B, a small basic peptide which is rapidly excreted by the kidneys, is known to react with and neutralize gram-negative bacterial endotoxins, specifically *E. coli* 0111:B4 liposaccharide (LPS) (Baldwin). It is not often administered parenterally as a treatment for septic shock syndrome, because high doses of polymyxin B are required for effective treatment. High doses can be fatal, due to renal toxicity, making advanced stages of septic shock difficult to treat.

The problem of rapid renal clearance observed with polymyxin B is also applicable to other small peptides, such as those discussed above, which have been used for parenteral treatment of disease. In general, circulating proteins which are smaller than about 50–60 Kdaltons will be cleared by the kidneys with a lifetime less than 1–2 hours.

In some cases, peptide molecular weight can be increased above the threshold 50–60 Kdalton size by derivatizing the peptide with biologically compatible polymers, such as polyethyleneglycol (PEG) (e.g., U.S. Pat. No. 4,179,337). However, this strategy may not always be effective for small effectors, e.g., those with molecular weights less than about 5–10 Kdalton. Moreover, derivatizing a polypeptide with a plurality of PEG chains may destroy or reduce the polypeptide activity, and/or mask key activity sites of the polypeptide.

4. SUMMARY OF THE INVENTION

The invention includes, in one aspect, a method of treating a subject by parenteral administration of a polypeptide or polysaccharide effector which is rapidly removed from the bloodstream by renal clearance in free form. The method includes parenterally administering to the subject, a liposome composition containing liposomes having an outer layer of polymer chains and the effector covalently attached to the distal ends of said chains. A preferred polymer is polyethylene glycol with chain lengths between about 1,000 and 10,000 daltons molecular weight.

Preferred effectors include:

(a) an antibody $F_{ab}$ fragment specific against a blood-circulating pathogen, for use in treating the subject for infection by the pathogen;

(b) a CD4 glycoprotein, for use in treating the subject for infection by human immunodeficiency virus (HIV);

(c) a cytokine or cellular growth factor, for use in stimulating an immune response in the subject;

(d) a mono or polysaccharide, such as sialyl Lewis$^x$, which binds to endothelial leukocyte adhesion molecule (ELAM), for use in treating a vascular inflammation related to neutrophil recruitment into sites of inflammation;

(e) IL-1 inhibitor or IL-1RA, for treating the subject to achieve immune-response suppression;

(f) polymyxin B, or polymyxin B decapeptide, for treating the subject for septic shock; and (g) a peptide hormone, for treating diseases subject to peptide hormone control.

In one specific embodiment, the invention includes a method of preventing progression of gram-negative bacteremia to septic shock and a method of treating acute septic shock by administering to a subject, a liposome composition containing liposomes having an outer layer of polyethylene glycol (PEG) chains and polymyxin B attached to the distal ends of the polymer chains.

In another aspect, the invention includes a composition of liposomes, each having an outer layer of polymer chains, typically polyethylene glycol chains, and one of the above effectors (a)–(g) attached to the distal ends of the chains.

These and other objects and features of the invention will become more fully apparent when the following detailed description of the invention is read in conjunction with the accompanying drawings.

BRIEF DESCRIPTION OF THE DRAWINGS

FIG. 10 shows the covalent coupling of a peptide, via a sulfhydryl group, to a disulfide linkage-containing propionamide of a DSPE carbamide of PEG bis (amine) maleimide of the DSPE carbamate of PEG bis (amine) shown in FIG. 2;

FIG. 11 shows the covalent coupling of a peptide, by reductive amination, to the aldehyde of an ethylene-linked derivative of DSPE carbamide of PEG (PEG), shown in FIG. 3.

DETAILED DESCRIPTION OF THE INVENTION

I. Definitions

Figure 1:
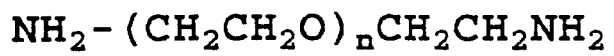
FIG. 1 shows steps for the synthesis of a maleimide of a DSPE carbamate of polyethylene glycol (PEG) bis (amine)
Figure 1:
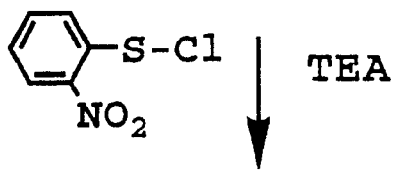
Figure 1:
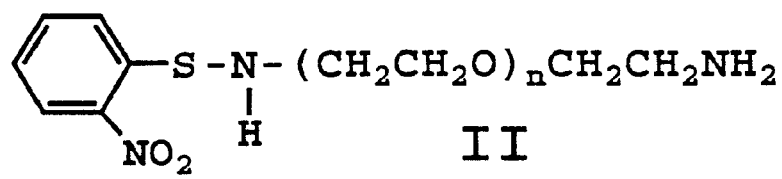
Figure 1:
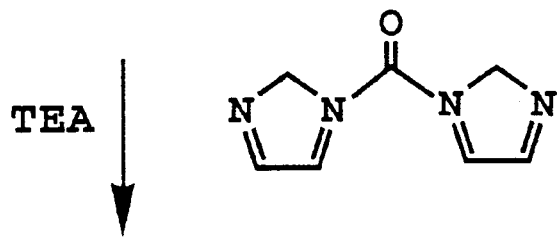
Figure 1:
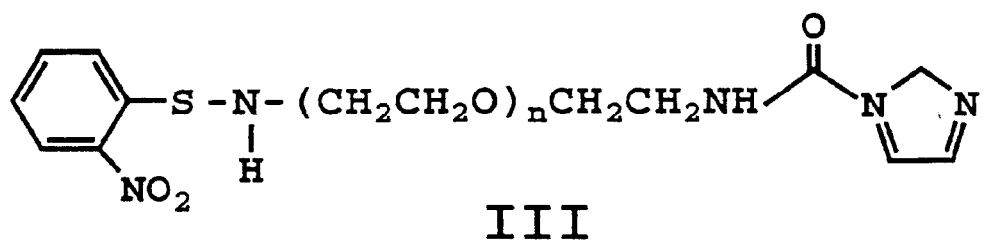

Unless otherwise indicated, the terms below have the following meaning:

"Vesicle-forming lipid" refers to any lipid capable of forming part of a stable micelle or liposome composition and typically including one or two hydrophobic acyl hydrocarbon chains or a steroid group and may contain a chemically reactive group, such as an amine, acid, ester, aldehyde or alcohol, at its polar head group.

"Effector" refers to polypeptides, mono or polysaccharides, and glycopeptides. Polypeptides, polysaccharides or glycopeptides may have sizes up to about 50–60 Kdaltons.

II. Effector Composition

The invention includes, in one aspect, a liposome composition for use in treating a subject with a small polypeptide or polysaccharide effector molecule which is itself, in free form, removed rapidly from the bloodstream by reanl clearance. The composition includes a liposomal carrier composed of liposomes having an outer layer formed of hydrophilic polymer chains, e.g., PEG. The effector is attached to the distal ends of the polymer in a portion of the derivatized vesicle-forming lipid. The effector is attached to distal end of a polymer chain to preserve the biological activity of the effector, such as behaving as a member of a ligand-receptor binding pair. The preparation of the composition follows the general procedures below.

A. Lipid Components

The liposomal carrier of the composition is composed of three general types of vesicle-forming lipid components. The first includes vesicle-forming lipids which will form the bulk of the vesicle structure in the liposome.

Generally, these vesicle-forming lipids include any amphipathic lipids having hydrophobic and polar head group moieties, and which (a) can form spontaneously into bilayer vesicles in water, as exemplified by phospholipids, or (b) are stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14–22 carbon atoms in length, and have varying degrees of unsaturation. The above-described lipids and phospholipids whose acyl chains have a variety of degrees of saturation can be obtained commercially, or prepared according to published methods. Other lipids that can be included in the invention are glycolipids and sterols, such as cholesterol.

The second general component includes a vesicle-forming lipid which is derivatized with a polymer chain which will form the polymer layer in the composition. The vesicle-forming lipids which can be used as the second general vesicle-forming lipid component are any of those described for the first general vesicle-forming lipid component. Vesicle forming lipids with diacyl chains, such as phospholipids, are preferred. One exemplary phospholipid is phosphatidylethanolamine (PE), which provides a reactive amino group which is convenient for coupling to the activated polymers. An exemplary PE is distearyl PE (DSPE).

The preferred polymer in the derivatized lipid, is polyethyleneglycol (PEG), preferably a PEG chain having a molecular weight between 1,000–10,000 daltons, more preferably between 2,000 and 5,000 daltons. Other hydrophilic polymers which may be suitable include polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

Additionally, block copolymers or random copolymers of these polymers, particularly including PEG segments, may be suitable. Methods for preparing lipids derivatized with hydrophilic polymers, such as PEG, are well known e.g., as described in co-owned U.S. Pat. No. 5,013,556.

The third general vesicle-forming lipid component is a lipid anchor by which the effector is anchored to the liposomes, through a polymer chain in the anchor. Additionally, the effector is positioned at the distal end of the polymer chain in such a way so that the biological activity of the effector is not lost. The lipid anchor has a hydrophobic moiety which serves to anchor the lipid in the outer layer of the liposome bilayer surface, a polar head group to which the interior end of the polymer is covalently attached, and a free (exterior) polymer end which is or can be activated for covalent coupling to the effector. Methods for preparing lipid anchor molecules of this types are described below.

B. Liposome Preparation

The liposomes may be prepared by a variety of techniques, such as those detailed in Szoka et al, 1980. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The lipids components used in forming the liposomes are preferably present in a molar ratio of about 70–90 percent vesicle forming lipids, 1–25 percent polymer derivatized lipid, and 0.1–5 percent lipid anchor. One exemplary formulation includes 50–70 mole percent underivatized PE, 20–40 mole percent cholesterol, 0.1–1 mole percent of a PE-PEG (3500) polymer with a chemically reactive group at its free end for effector coupling, 5–10 mole percent PE derivatized with PEG 3500 polymer chains, and 1 mole percent α-tocopherol.

The liposomes are preferably prepared to have substantially homogeneous sizes in a selected size range, typically between about 0.03 to 0.5 microns. one effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin).

C. Effector Component

The effector in the composition is a therapeutic polypeptide, mono or polysaccharide, or glycopeptide characterized, when administered intravenously in free form, by rapid clearance from the bloodstream, typically within 1–2 hours. Below are described preferred effectors for use in the invention.

1. $F_{ab}$ Fragment. The $F_{ab}$ fragment is one which has neutralizing activity against a given pathogen. The composition is used as a passive vaccine effective to provide humoral immunity against one of a variety of selected pathogenic antigens.

$F_{ab}$ fragments of neutralizing antibodies can be prepared according to conventional methods (Harlow). The fragment is preferably from a humanized monoclonal antibody ($M_{ab}$). Such antibodies can be prepared by published recombinant DNA methods (Larrick). The antibody is preferably coupled to liposomal hydrophilic polymer groups via sulfhydryl linkages, as described above.

2. CD4 Glycoprotein Effector. The CD4 glycopeptide is a region of the CD4 receptor of CD4+ T cells (Capon). The effector acts to block HIV infection of CD4+ T cells by blocking gp120-mediated HIV binding to the CD4 receptor. The effector can be produced according to known recombinant methods (Maniatis).

3. Cytokines. The cytokines given in Table 1 below are examples of cytokines which are useful in the present invention. The cytokines may be obtained by recombinant production methods, according to published procedures. The therapeutic uses of the individual cytokines have been described in the literature (see, for example, Abbas). Some cytokine effectors may be administered on a short term basis to enhance a weak immunogenic or weak microbicidal response. The effectors may be administered on a long term basis as part of a therapy treatment for cancer or AIDS (Waldmann).

TABLE 1

| CYTOKINE | POLYTPEPTIDE SIZE |
|---|---|
| A. Mediators of Natural Immunity | |
| IFN-alpha | 18 kD (monomer) |
| IFN-beta | 20 kD (monomer) |
| Tumor necrosis factor (TNF) | 17 kD (homotrimer) |
| Interleukin-1 (alpha and beta) | 17 kD (monomer) |
| Interleukin-6 | 26 kD (monomer) |
| Interleukin-8's | 8–10 (monomer or dimer) |
| B. Mediators of Lymphocyte Activation, Growth and Differentiation | |
| Interleukin-2 | 14–17 kD (monomer) |
| Interleukin-4 | 20 kD (monomer) |
| Transforming growth factor (beta) | 14 kD (monomer or dimer) |

TABLE 1-continued

| CYTOKINE | POLYTPEPTIDE SIZE |
|---|---|
| C. Mediators of Effector Cell Adhesion | |
| Gamma Interferon | 21–24 kD (homodimer) |
| Lymphotoxin | 24 kD (homotrimer) |
| Interleukin-5 | 20 kD (monomer) |
| D. Mediators of Immature Leukocyte Growth and Differentiation | |
| Interleukin-3 | 20–26 kD (monomer) |
| Granulocyte-macrophage Colony Stimulating Factor | 22 kD (monomer) |
| Macrophage Colony Stimulating Factor | 40 kD (dimer) |
| Granulocyte CSF | 19 kD (monomer) |
| Interleukin-7 | 25 kD (monomer) |

4. ELAM-1 Binding Inhibitor. Inflammation causes the expression of a polypeptide, endothelial leukocyte adhesion molecule-1 (ELAM-1), on the surface of endothelial cells of blood vessels, adjacent to sites of inflammation. ELAM-1, in turn, recognizes and binds a polysaccharide moiety, sialyl Lewis$^x$ on surfaces of neutrophils, and recruits neutrophils to sites of inflammation. By preventing the recognition and binding of neutrophils by ELAM-1, excessive inflammatory responses due to conditions, such as reperfusion injury, septic shock, and chronic inflammatory diseases, can be avoided.

In this embodiment, the effector is the tetrasaccharide, sialyl Lewis$^x$, recognized by ELAM-1 (Phillips), for therapeutical use in preventing excessive recruitment of neutrophils to sites of inflammation in the blood stream. The effector is produced by the glycosylation mutants of Chinese hamster ovary (CHO) cells, and may be obtained in purified form from the cultured cells (Phillips). Alternatively, the effector is produced by chemical and/or enzymatic synthesis (Borman, Ichikawa).

5. Inhibitors of IL-1 Activity. The effector in this embodiment is an IL-1 inhibitor, or IL-1 receptor antagonist (IL1RA), which blocks binding of IL-1 to receptors on lymphocyte cell surfaces (Stylianou).

IL-1 production is stimulated by both endotoxins which cause septic shock and exotoxins which cause toxic shock syndrome (Dinarello). IL-1 production during septic shock or toxic shock may exacerbate the clinical symptoms observed in patients. Therefore, use of an IL-1 inhibitor effector to decrease the clinical symptoms associated with either toxic shock or septic shock may be beneficial.

IL-1 inhibitor is a 52 to 66 Kd polypeptide that binds specifically to IL-1 to inhibit its immunostimulatory responses. IL1RA is a 23 to 25 KD polypeptide that competes with binding of IL-1 to its cell surface receptors to inhibit IL-1's immunostimulatory responses.

6. Polymyxin B. This effector is a cationic detergent with a hydrophobic portion (6-methyloctanoyl) and a short basic decapeptide portion. Polymyxin B reacts with and neutralizes gram-negative bacterial endotoxins, specifically E. coli 0111:B4 liposaccharide (LPS) (Baldwin). Polymixin B is used in the treatment of gram-negative bacterial infections. Since polymyxin B must be administered frequently and in high doses because of its rapid clearance from the bloodstream, it causes severe irreversible kidney damage. Polymyxin B can be chemically synthesized or isolated from spore-forming gram-positive bacilli, such as Bacillus polymyxa.

Alternatively, the effector is an 11.8 Kdalton peptide isolated from amebocytes of Limulus polyphemus, limulus antilipopolysaccharide factor (LALF). LALF neutralizes meningococcal lipooligosaccharide, as well as other gram-negative endotoxins, and can be used to treat gram-negative sepsis (Wainwright).

7. Peptide Hormone. This effector can be used in the treatment of various diseases. In one embodiment, the effector is parathyroid hormone (PTH) which is 84 amino acids in length and can inhibit osteoblast division. Certain bone cancers are characterized by uncontrolled osteoblast division (Kano). Alternatively, the peptide hormone can be used to target a liposome to cells that contain receptors for a specific peptide hormone.

D. Attachment of Effector to Liposome Carrier

For effector attachment to liposome carriers the free polymer end of a lipid anchor is activated prior to effector coupling. In the following specific examples, both lipid anchor formation and activation reactions are described. The reactions are shown with respect to the free lipid, distearylphosphatidylethanolamine (DSPE). The activated lipid anchors are then incorporated into liposomal carriers, as described above.

One advantage of activating the PEG terminal group of the lipid anchor prior to liposome formation is that a broader range of reaction solvents and reaction conditions may be employed. Further, the liposomes themselves are not exposed to the activating reagents. Thus, the need to remove reagent contaminants from the liposomes is avoided.

It will also be appreciated that the activation reactions may be performed after lipid anchor incorporation into liposomal carriers. In some coupling reactions it may be more desirable to activate the terminal PEG groups on preformed liposomes. One advantage of this approach is that the activation reaction is confined to the outer, surface-accessible lipids, and thus the activated groups can be completely quenched prior to use of the composition in therapy. The approach is also preferred for reactions in which the activated PEG termini are unstable in water.

FIG. 1 shows the synthesis of a DSPE derivatized with a PEG chain and having an activated chemical group at the chain's free end. Initially, PEG bis (amine) (compound I) is reacted with 2-nitrobenzene sulfonyl chloride to generate the monoprotected product (compound II). Compound II is reacted with carbonyl diimidazole in triethylamine (TEA) to form the imidazole carbamate of the mono 2-nitrobenzenesulfonamide (compound III).

Compound III is reacted with DSPE in TEA to form the derivatized PE lipid protected at one end with 2-nitrobenzyl sulfonyl chloride. The protecting group is removed by treatment with acid to give the DSPE-PEG product (compound IX) having a terminal amine on the PEG chain. Reaction with maleic acid anhydride gives the corresponding maleamic product (compound V), which on reaction with acetic anhydride gives the desired PE-PEG-maleimide product (compound VI). Details of the reactions are given in Example 1.

Figure 8:
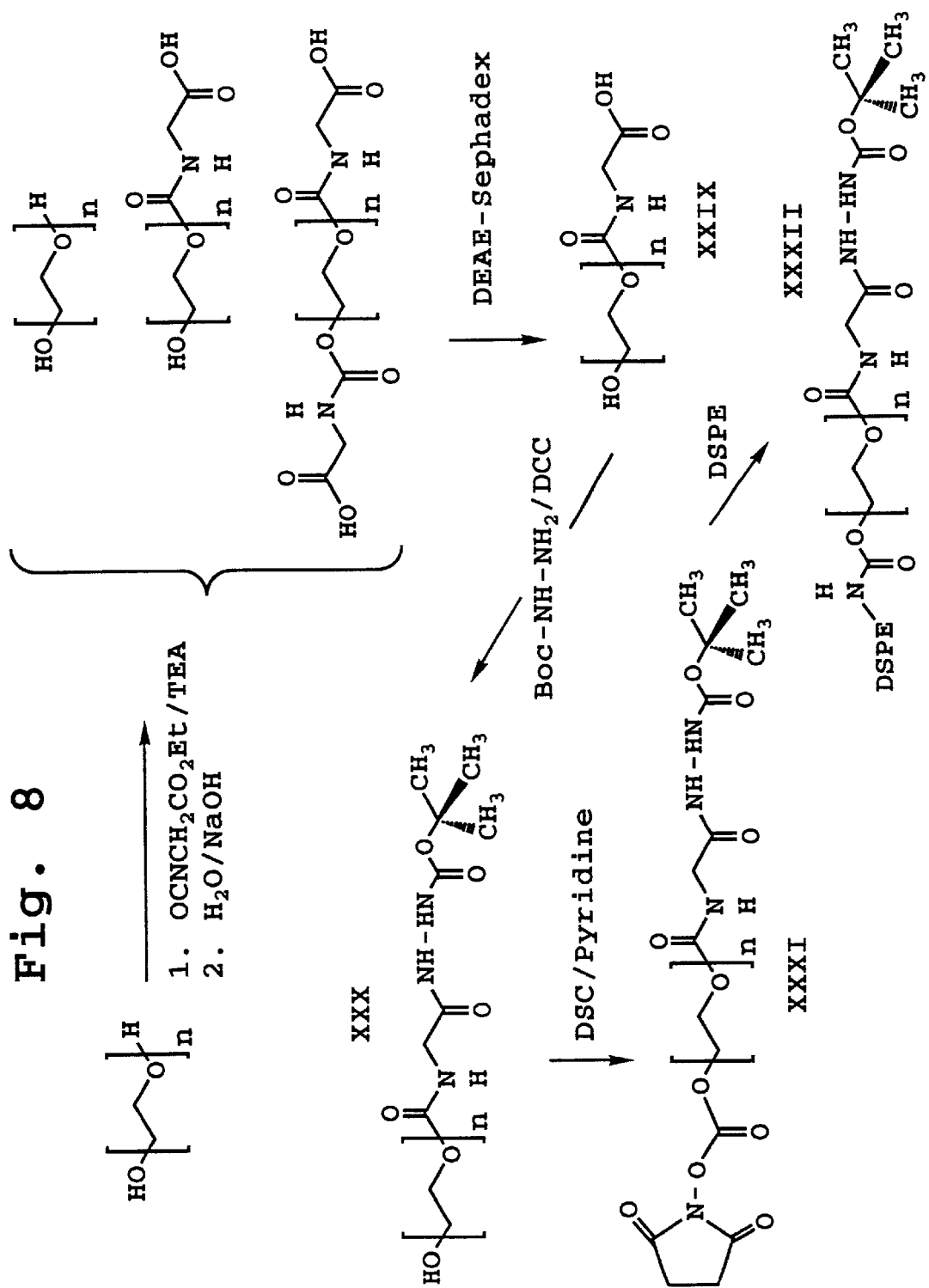
FIG. 8 shows steps in forming another PE derivatized by a PEG spacer chain having a hydrazide group.

The compound is reactive with sulfhydryl groups, for coupling polypeptides through a thioether linkage, as illustrated in FIG. 8.

Figure 2:
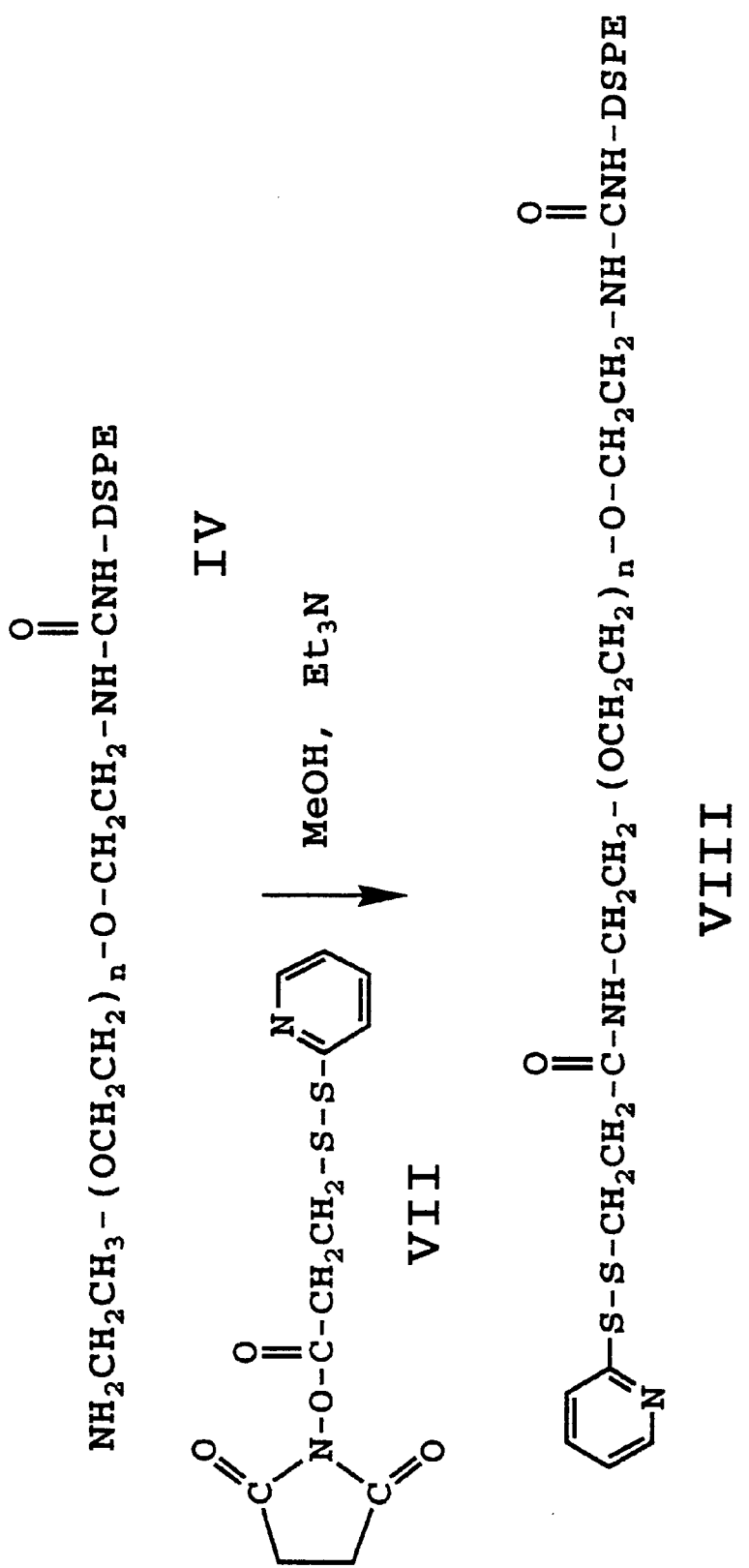
FIG. 2 shows steps for the synthesis of a disulfide linkage-containing propionamide of a DSPE carbamide of polyethylene glycol (PEG) bis (amine)

FIG. 2 illustrates the synthesis of another derivatized lipid useful for coupling sulfhydryl-containing polypeptides to the polymer terminal end of the derivatized lipid. Here the PE-PEG (compound IV) from above is treated with N-succinimidyl-3-(2-pyridyldithio)propionamide (compound VII) to form the anchor lipid PE-PEG (compound VIII). The compound can react with a sulfhydryl group of a peptide to couple peptide to the lipid through a disulfide linkage as illustrated in FIG. 10.

Figure 3:
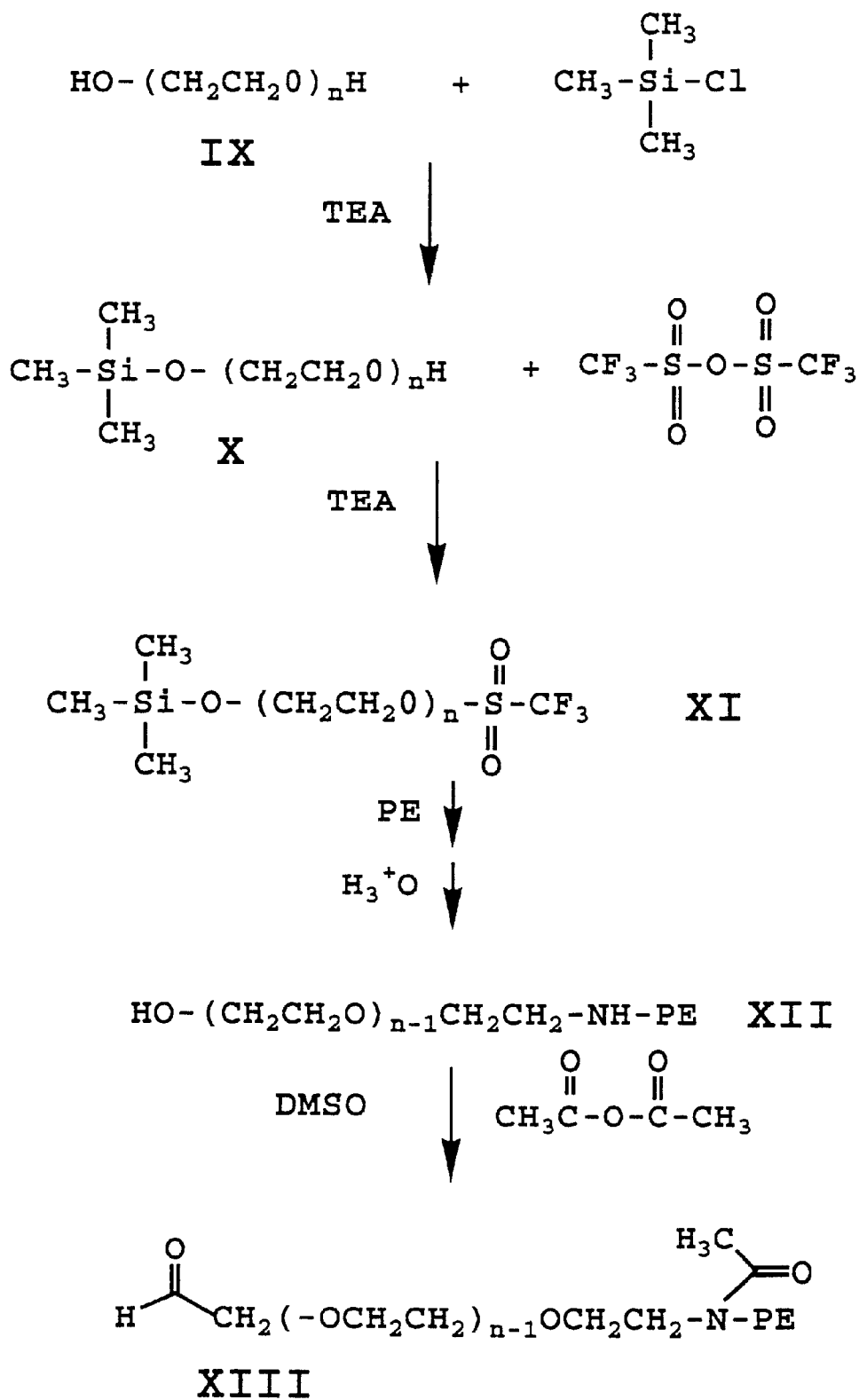
FIG. 3 shows the synthetic scheme for the preparation of an aldehyde of an ethylene-linked PEG derivative of DSPE.

Another reaction method for coupling a protected polyalkylether to a lipid amine is shown in FIG. 3. In this reaction scheme, PEG (compound IX) is initially protected at one of its terminal OH ends by a trimethylsilane group, as shown at the top in FIG. 5. The protected PEG (compound X) is reacted with the anhydride of trifluoromethyl sulfonate to activate the free PEG end with trifluoromethyl sulfonate (compound XI). Reaction of the activated compound with a lipid amine, such as PE, in the presence of triethylamine, and release of the trimethylsilyl protective group by acid treatment, gives the PE-PEG derivative (compound XII) containing a terminal alcohol group which is oxidized in the presense of dimethylsulfoxide (DMSO) and acetic anhydride to convert the terminal OH to an aldehyde group (compound XIII) which can be coupled to a peptide via reductive amination, as illustrated in FIG. 10. Reaction details are given in Example 2.

More generally, the derivatized lipid components can be prepared to include a lipid-polymer linkage, such as a peptide, ester, or disulfide linkage, which can be cleaved under selective physiological conditions, such as in the presence of peptidase or esterase enzymes or reducing agents, such as glutathione, present intracellularly.

Figure 4:
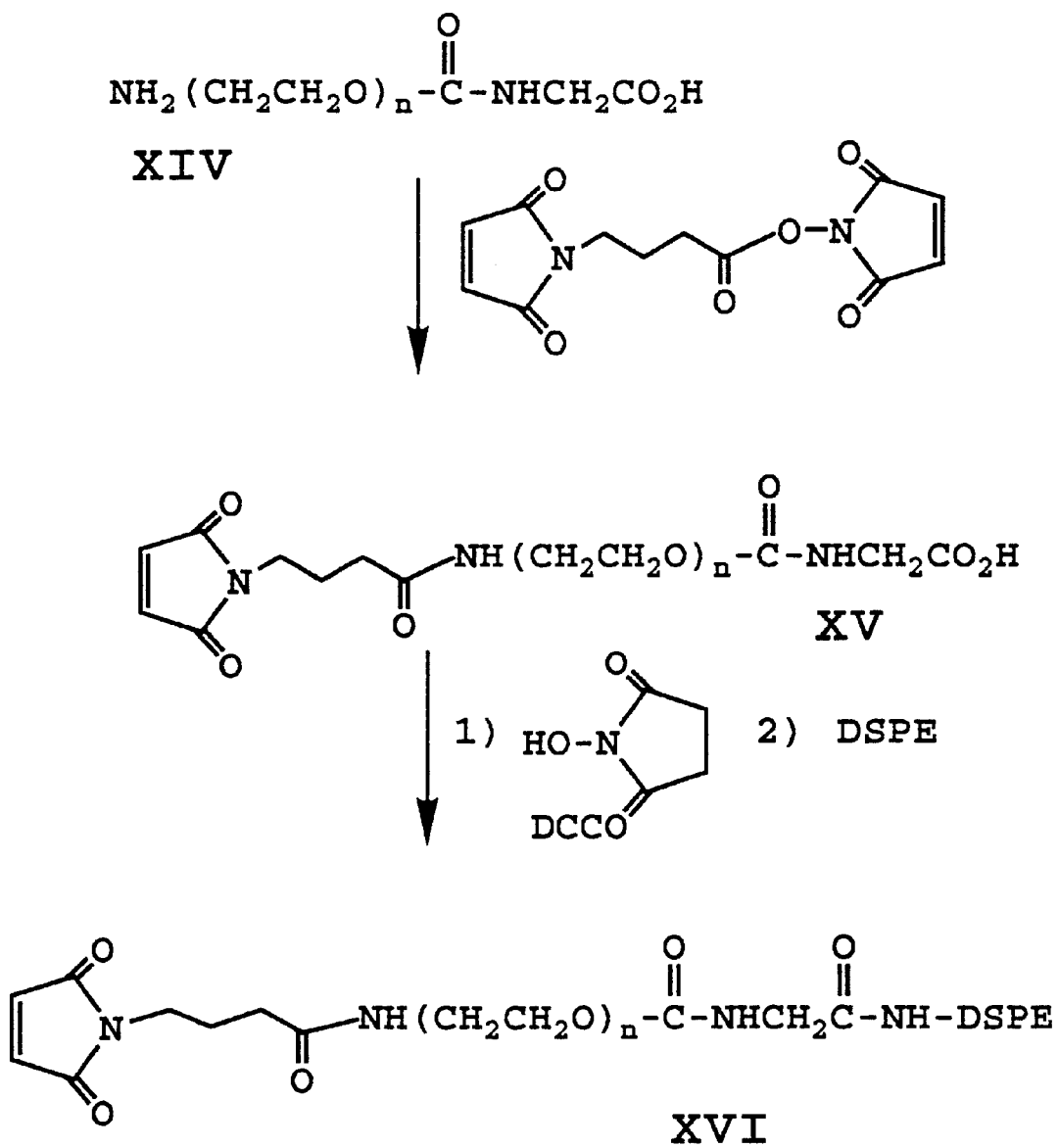
FIG. 4 illustrates steps in the formation of a PEG-derivatized PE having a maleimide group at the polymer end.
Figure 5:
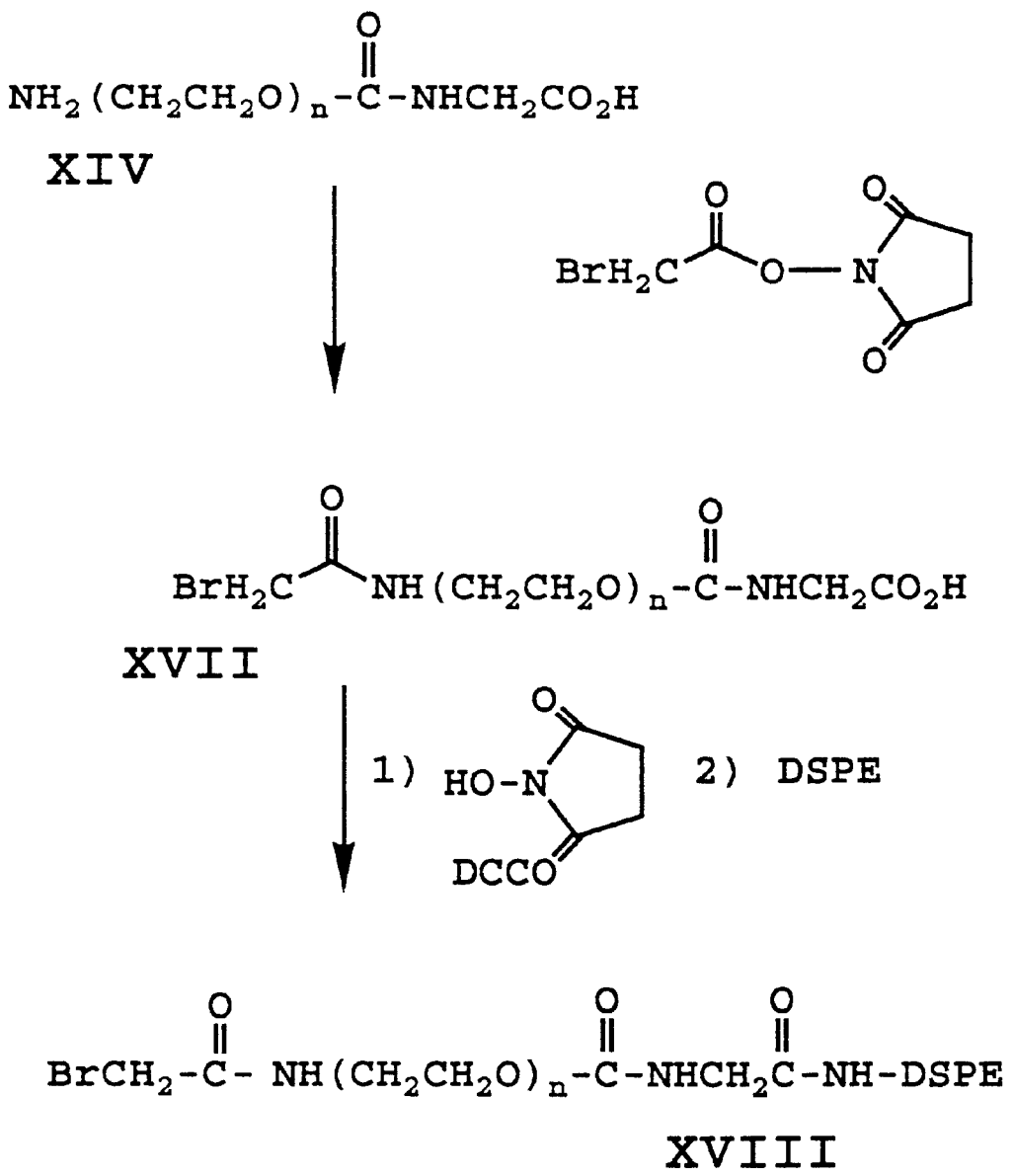
FIG. 5 illustrates steps in the formation of a PEG-derivatized PE having a bromoacetamide group at the polymer end.

An alternative general method for preparation of lipid derivatives of PEG suitable for coupling to effector molecules involves omega-amino carboxylic acids of PEG (such as compound XIV) as starting material and is illustrated in FIGS. 4 and 5. Methods for preparing such heterobifunctional PEG derivatives have been described by Zalipsky, et al., (1986; 1990). In the FIG. 4 reaction scheme, an omega-amino carboxylic acid of PEG (Zalipsky, et al., 1986) is reacted with maleimido propionate N-hydroxysuccinimide ester (MPS, Pierce), using an excess of MPS. The carboxyl group of the resulting maleimido-PEG (compound XV) is then reacted with a lipid amine, such as PE, in the presence of N-hydroxysuccinimide, to link the PEG to the lipid through an amide linkage (compound XVI). The maleimido group at the "free" end of the polymer is reactive towards thiol-containing ligands, proteins, e.g., immunoglobulins and fragments thereof. A related scheme is illustrated in FIG. 5, which shows initial formation of a terminal bromoacetamide group on a PEG carboxylic acid (compound XVII), by reacting an omega-amine carboxylic acid of PEG (compound XIV) with bromoacetyl N-hydroxysuccinimide ester. The PEG is then coupled to a suitable lipid amine, such as PE, as above, to form the derivatized lipid (compound XVIII). The bromoacetamide group, being more selective and more stable than a maleimide group, will allow more flexibility in the methods used for liposome formation and loading.

Figure 6:
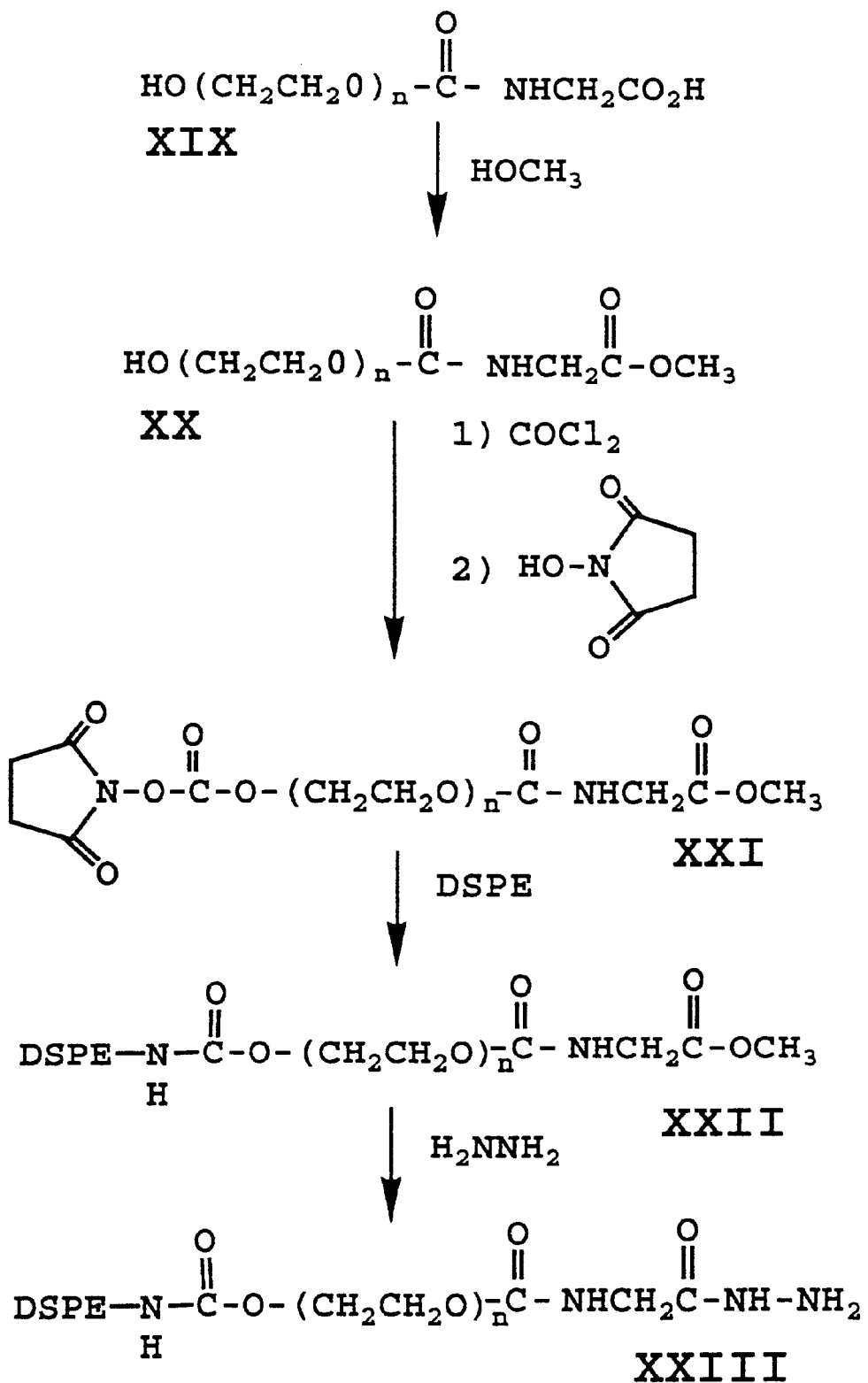
FIG. 6 shows steps in the synthesis of a derivatized DSPE lipid having a PEG terminal hydrazide group.
Figure 7A:
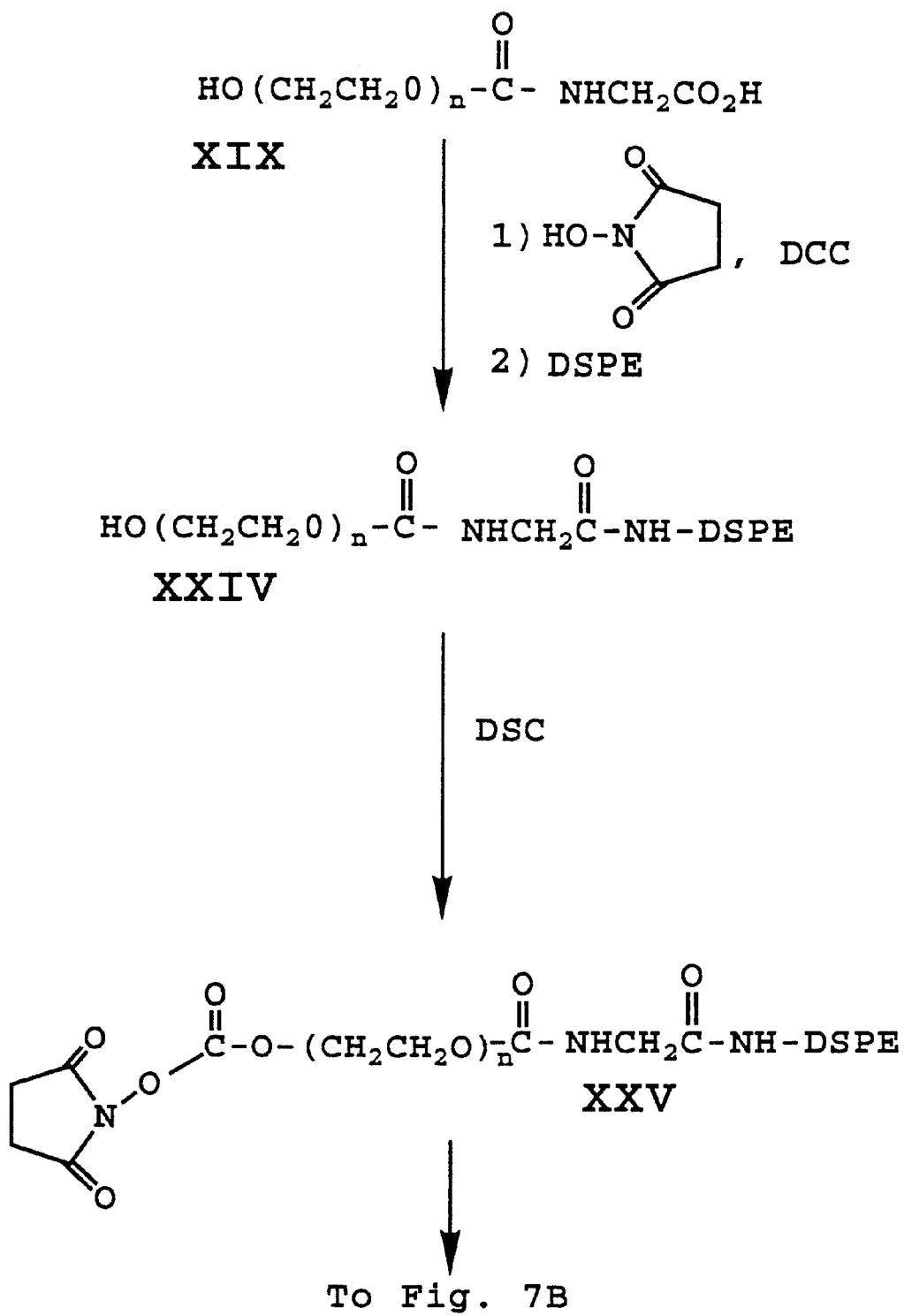
FIGS. 7A–7D show steps in the synthesis of a derivatized DSPE lipid having a PEG terminal activated group (7A) which can be used to couple a variety of amine-containing groups (7B–7D) to the PEG polymer ends.

The reaction scheme shown in FIG. 6 is for the preparation of a derivatized lipid in which the free PEG end is an OH group (omega OH group). In the reaction illustrated in FIG. 6, the omega-hydroxy carboxylic acid of PEG (compound XIX) (Zalipsky, 1990) is esterified with methanol, to protect the terminal acid group (compound XX). The terminal hydroxyl group is then converted into a functional group reactive towards primary amines (Zalipsky, 1992a), for example, a succinimidyl carbonate (SC) derivative (compound XXI). This compound is formed by reacting compound XX with phosgene, with subsequent reaction with N-hydroxysuccinimide (Zalipsky, 1992b). The resulting SC-PEG-CO$_2$-Me (XXI) reacts with a lipid amine, such as DSPE, to form the DSPE-PEG-CO$_2$-Me (compound XXII). The methyl ester can be cleanly hydrazinolyzed to yield PE-PEG-CO-N$_2$H$_3$ (compound XXIII), as shown. This hydrazide-containing PEG-lipid is incorporated into liposomes by conventional methods. The hydrazide group can be used for attachment of aldehyde or ketone containing effector molecules. Such carbonyl groups exist or can be easily generated on numerous carbohydrate containing molecules, e.g. oligosaccharides, nucleotides, low molecular weight glycosides, lectins, immunoglobulins and other glycoproteins by chemical (periodate oxidation) or enzymatic reactions (galactose oxidase). The linkages formed, hydrazones, are reasonably stable at pH$\geq$7.5, but are cleavable by acid catalyzed hydrolysis at lower pH values. These linkages can be stabilized by reduction, e.g., with sodium cyanoborohydride. An advantage of this approach is the stability of hydrazide groups which will allow for the use of a wide array of liposome formulations and loading protocols. Alternatively, as illustrated in FIG. 7A, the ω-hydroxy carboxylic acid of PEG (compound XIX) can be used for reaction with amino groups of PE derivatives, can be initially coupled to the amine lipid, e.g., DSPE, to form the derivatized lipid (compound XXIV). The terminal OH group of this conjugate can be activated, for example, with disuccinimidyl carbonate (DSC), to form SC-PEG-DSPE (compound XXV) for selective reactions with a variety of amino-group containing compounds. Chemical reactions are described in Example 4. These amino-group containing compounds will also possess at least one other functional group to which numerous effector molecules may be attached. The attachment of the effector molecules may occur before or after liposome formation.

Figure 7B:
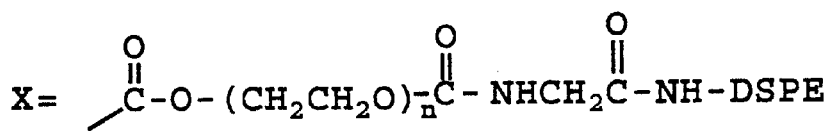
Figure 7B:
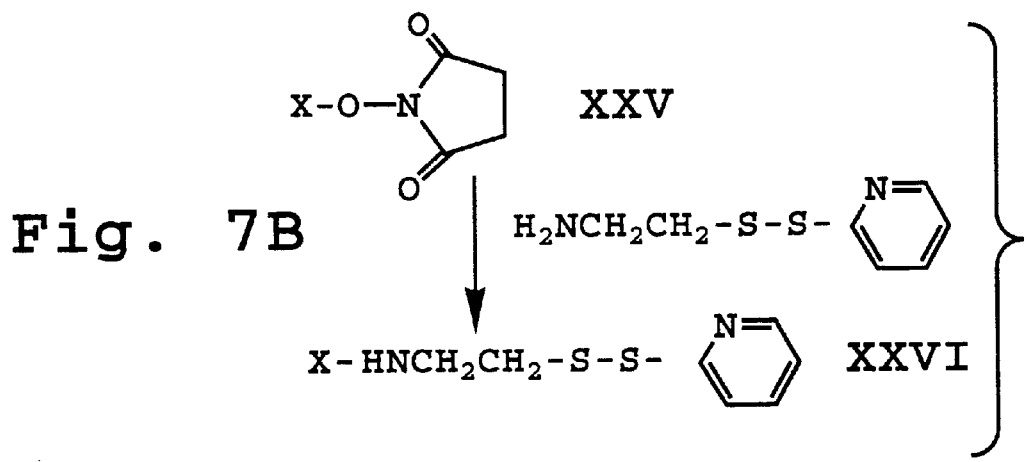

In one case, as illustrated in FIG. 7B, the SC-PEG-DSPE is reacted with 2-aminoethanedithiopyridine. The derivative formed (compound XXVI) can be used in two ways. The dithiopyridine group is reactive towards thiol-containing molecules and it is quite stable in a variety of conditions. Using mild reducing agents, e.g., β-mercaptoethanol, it is possible to convert the dithiopyridine groups on the liposomes into free thiols, which in turn can be used in various conjugation procedures involving ligands containing alkylating maleimido or bromoacetate groups or reactive mixed disulfide groups like dithiopyridine.

Figure 7C:
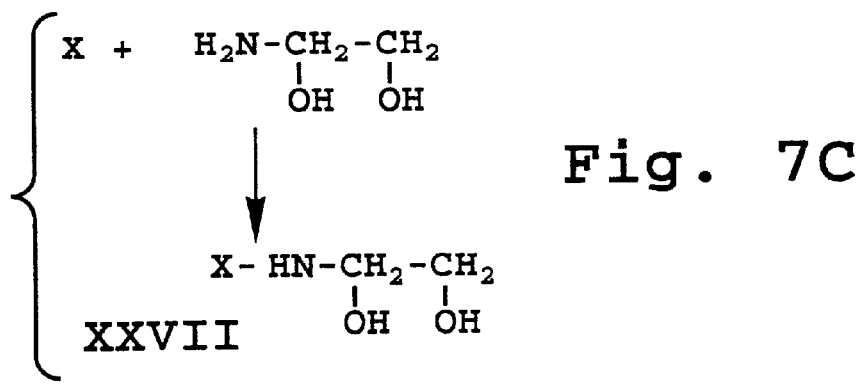

In the reaction illustrated in FIG. 7C, the SC-PEG-DSPE is reacted with aminopropanediol, producing a diol terminated PEG-lipid (compound XXVII). After incorporation into a liposome, the diol can be oxidized with periodate under mild conditions ([IO$_4$-]$\leq$10 mM, 4° C.) to provide a reactive aldehyde. The aldehyde containing PEG-liposomes will react irreversibly with a variety of amino-containing effector molecules in the presence of sodium cyanoborohydride.

Figure 7D:
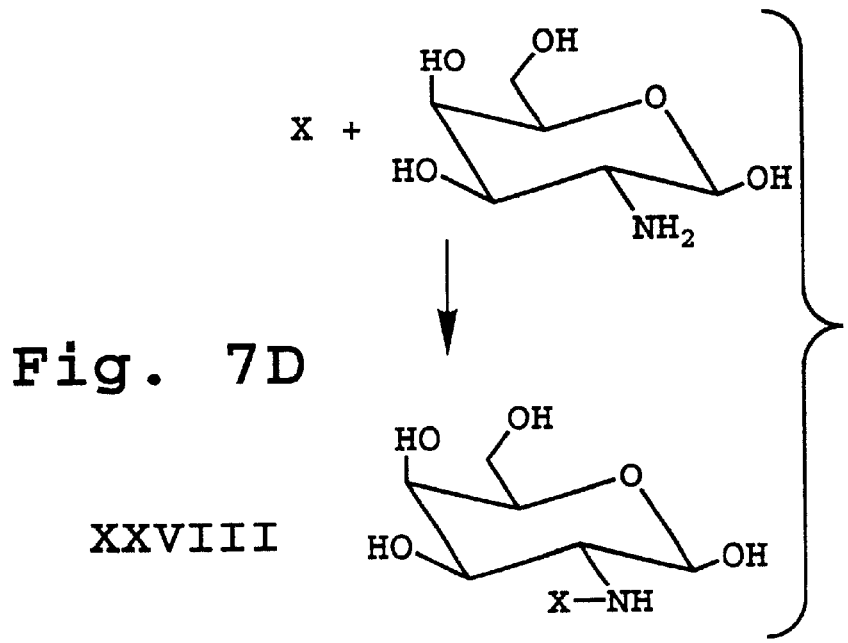

In the reaction illustrated in FIG. 7D, SC-PEG-DSPE is coupled to a galactosamine. The galactose residue on the derivatized lipid (compound XXVIII) can then be enzymatically oxidized by galactose oxidase. The aldehyde bearing PEG-liposomes obtained by this process can be used for conjugation with amino-group containing effector molecules. In addition to the mildness of the reaction conditions, the aldehyde groups are solely generated on the outer surface of the liposome.

Additionally, there is evidence that oxidized galactose residues are useful for stimulation of the immune system, specifically for T cell activation. A liposome having oxidized galactose residues on its surface is likely to act as an adjuvant and might be useful in vaccines (Zheng).

In a another procedure, illustrated in FIG. 8 and described in Example 5, DSPE-PEG-hydrazide is prepared. First PEG is reacted with ethyl isocyanatoacetate in the presence of triethylamine to generate mono and dicarboxylated species of PEG. The monocarboxylated species is purified by ion-exchange chromatography on DEAE-Sephadex (compound XXIX, identical to compound XIX). Compound XXIX is reacted with tert-butyl carbazate to generate the hydroxy Boc-hydrazide derivative of PEG (compound XXX). The free hydroxyl group is activated by reaction with disuccinimidyl carbonate to activate the terminal hydroxyl group (compound XXXI) prior to reaction with DSPE to generate product (compound XXXII). Compound XXXII is deprotecccted with 4M HCl in dioxane exposing the free hydrazide group. Lipid-PEG-hydrazide is the incorporated into liposomes. These hydrazide groups are reactive towards aldehydes, which as described above can be generated on numerous biologically relevant compounds.

The methods just described may be applied to a variety of lipid amines, including PE, cholesteryl amine, and glycolipids with sugar amine groups. It will be appreciated that a variety of alternative coupling reactions, in addition to those just described, are suitable for preparing vesicle-forming lipids derivatized with hydrophilic polymers such as PEG, having terminal groups which are activated or are reactive in protein coupling reactions.

1. Maleimide Coupling. Maleimides are widely used protein modifying reagents and are especially useful when the maleimide is one of two functional groups in a heterobifunctional crosslinking reagent. The reaction of maleimides with sulfhydryl groups involves Michael addition of the mercaptane group to the activated double bond. Reaction with amino groups occurs by the same mechanism, but at a much slower rate. Since mercaptane is the most reactive species, particularly at neutral pH, the maleimide group can be used to target a small number of sulfhydryl groups and good selectivity is usually acheived.

Figure 9:
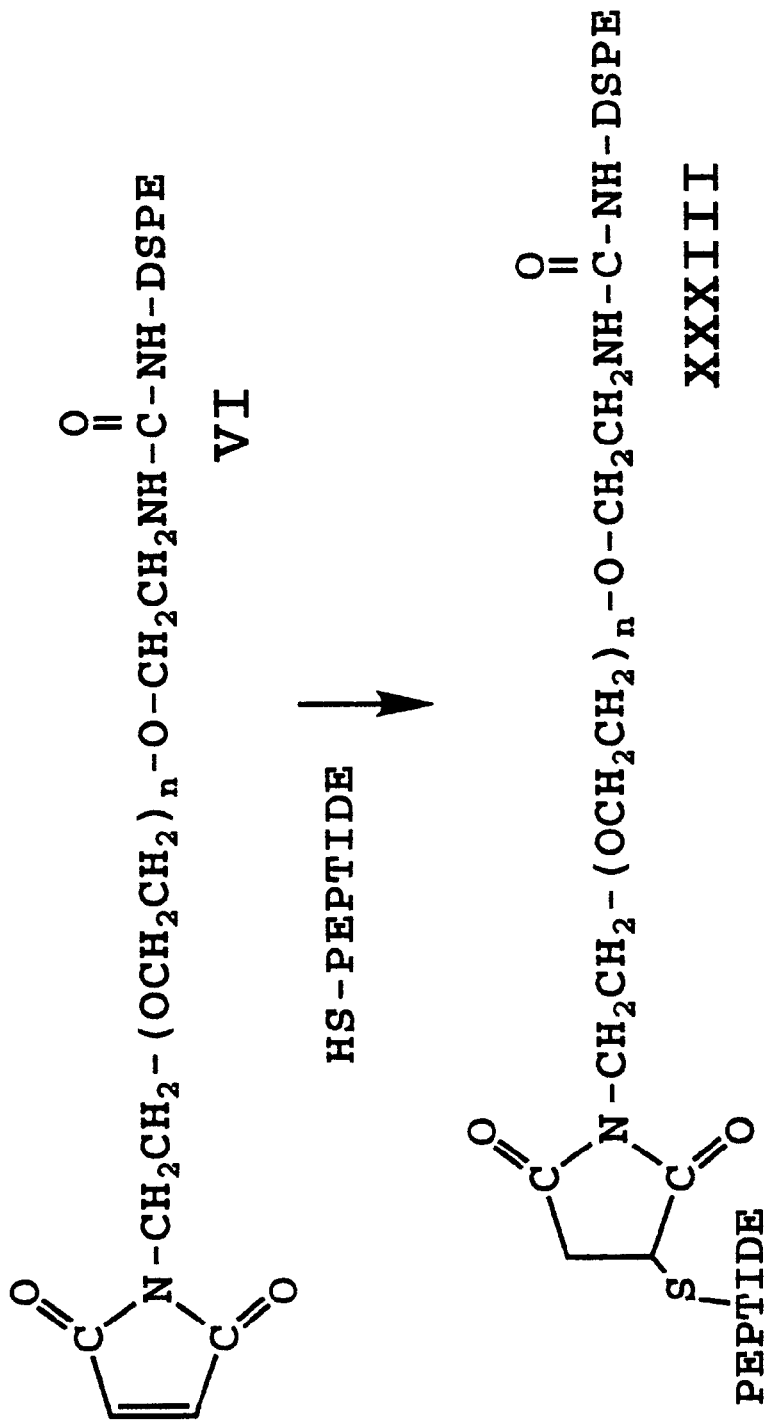
FIG. 9 shows the covalent coupling of a peptide, via a sulfhydryl group, to the maleimide of a DSPE carbamate of PEG bis (amine) shown in FIG. 1.
Figure 12:
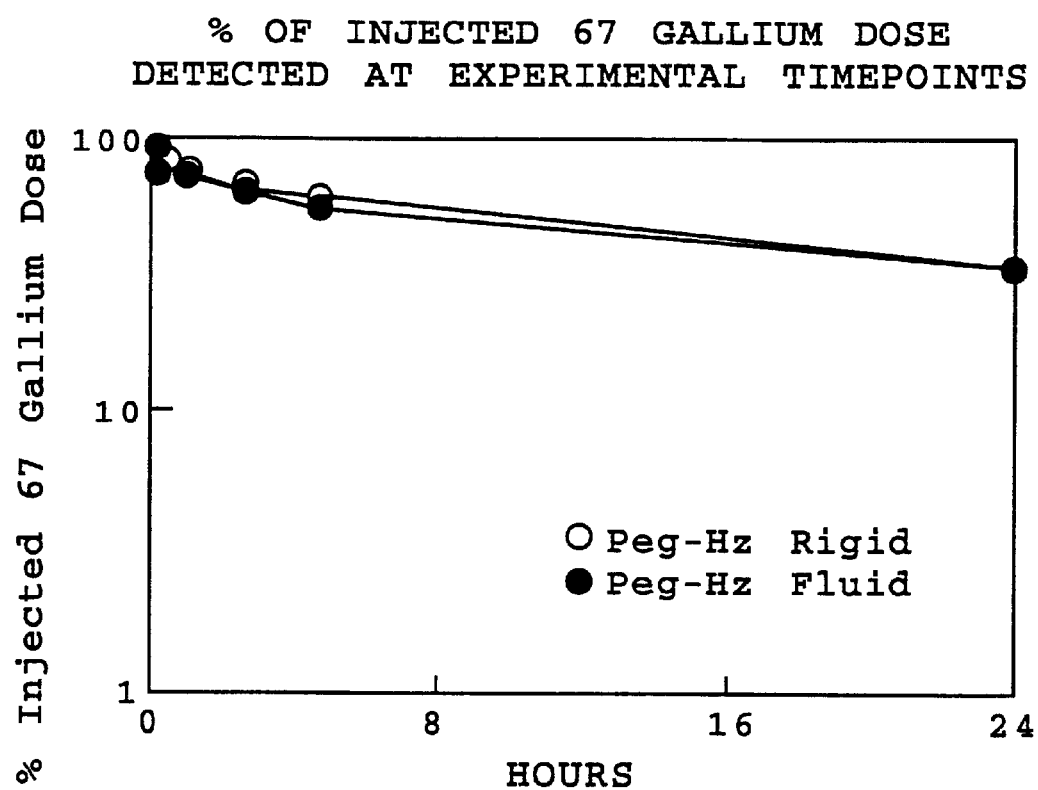
FIG. 12 shows a plot of a time course of gallium-67 labelled liposomes composed of hydrazide PEG-DSPE, partially hydrogenated egg phosphatidylcholine (PHEPC), and cholesterol (PEG-HZ fluid liposomes) or hydrazide PEG-DSPE, hydrogenated serum phophatidylcholine (HSPC), and cholesterol (PEG-HZ rigid liposomes) in the bloodstream.

In one preferred embodiment, a derivatized lipid, such as PE-PEG, is formed with a terminal maleimide group (compounds VI and XVI), as illustrated in FIGS. 1 and 4 above. The lipid, after incorporation into liposomes, is then reacted with a sulfhydryl-containing effector, typically a polypeptide, under suitable coupling conditions. The reaction of the maleimide lipid (compound VI or XVI) with a peptide sulfhydryl group is illustrated in FIG. 9. As shown, the reaction couples the protein to the lipid polymer through a thioether linkage, to give the derivatized PE (compound XXXIII). Use of the reaction to couple proteins to liposomes is described in Example 6.

In this example the efficiency of β-galactosidase coupling to liposomes containing a maleimide coupling agent in the presence or absence of PE-PEG3500 is compared. The reactions were carried out with liposomes prepared to contain, as the maleimide coupling agent, either (a) the DSPE derivative of succinimidyl 4-(p-maleimidophenyl) butyrate (MBP), (b) the DSPE derivative of N-(11-maleimido-undecanoyl) (C11), or (c) the maleimide of PE-PEG3500.

After the coupling reaction, performed as described above for (a)–(c), the amount of liposome-bound enzyme was quantitated. Recovery of liposomes was measured by scintillation counting and the recovery of protein was measured by the beta-galactosidase assay and direct quantitation of the protein amount. The maleimide of the DSPE carbamide of PEG3500 was very effective in crosslinking β-galactosidase to liposomes, either in the presence or absence of PE-PEG3500 chains. As seen in Table 2, there was essentially no difference in the amount of protein crosslinked to either type of liposome in two separate experiments. In addition, the amount of protein coupled to the PE-PEG maleimide was much higher than to either the MPB or MPB-$C_{11}$ maleimides.

The presence of "non-activated" PE-PEG3500 in the liposomes had little effect on the levels of coupling of the protein to PE-PEG-maleimide liposomes, but inhibited the level of protein coupling to liposomes containing either the MPB lipid, or the MBP-$CL_{11}$ lipid.

TABLE 2

| "Phenotype" | | | ng Protein/ |
| --- | --- | --- | --- |
| PEG-DSPE | Crosslinker | 10 mM 2-ME | µmol Lipid* |
| − | MPB | | 1609/2284 |
| − | MPB | + | (−80) |
| + | MPB | | (−282) |
| − | $C_{11}$ | | 690 |
| − | $C_{11}$ | + | 847 |
| + | $C_{11}$ | | 358 (−157) |
| + | $C_{11}$ | + | 80 |
| − | 3500 | | 10,033 |
| − | 3500 | + | 572 |
| + | 3500 | | 10,765/12,412 |
| + | 3500 | + | 110 |

*Background binding in the absence of crosslinker has been subtracted. Background values range from 500–1000 ng protein/µmol lipid. There was a tendency for background values to be somewhat (10–30%) higher in the presence of PEG-DSPE; this may not be significant. Multiple entries denote multiple separate crosslinking experiments.

2. Coupling by 3-(2-pyridyldithio) propionamide. The reaction of dithio propionamides with the sulfhydryl group produces coupling to the sulfhydryl-containing molecules via a disulfide linkage. Disulfide exchange occurs readily at pH 8, in a nonreducing environment. The method involves reaction of a thiol group in a peptide with a liposome prepared to contain PE-PEG (2-pyridyldithio) propionamide). The reaction couples the protein to the liposomes through a disulfide linkage as illustrated in FIG. 10 (compound XXXIV).

3. Reductive amination. In this procedure, the terminal hydroxyl group of a PEG chain, covalently linked at one end to PE, is converted to the aldehyde by mild oxidation. The oxidation step may be carried out before or after incorporation into liposomes to produce the aldehyde form of the derivatized lipid (compound XIII in FIG. 3). Reaction of the aldehyde with the amine group of an effector molecule gives the Schiff base (compound XXXV) which is then reduced to the desired derivatized lipid with amine-group linked peptide (XXXVI).

As indicated above, the polymers can also be activated for effector coupling in preformed lipids, i.e., with the polymer-derivatized lipids already incorporated into liposomes. One advantage of this approach is that only polymer moieties on the outer surface of the liposomes are activated. In one general approach, involving PEG polymers, the terminal OH groups are first oxidized by treatment with sodium periodate for 2 hours at 20° C. in the dark. After oxidation, the excess reagent is removed, and the liposomes are incubated with the effector molecule, e.g. $F_{ab}$ fragments, in the presence of 2M sodium cyanoborohydride (10 µl/ml) at 20° C. for 14 hours. After completing the incubation, the liposomes were chromatographed on a Sepharose to remove free (non-linked) effector molecules.

III. Bloodstream and Tissue Retention of Liposomes Containing End-Functionalized PEG-DSPE In vivo studies were undertaken to determine the bloodstream and tissue retention of liposomes containing end-functionalized PEG-DSPE. End-functionalized PEG-DSPE contains a chemically active group which can be used for attaching a variety of compounds to liposomes. From these studies it has been determined that end-functionalization does not affect the extended lifetime in the bloodstream of liposomes containing PEG-DSPE, monomethoxy PEG-DSPE, or other similarly modified vesicle-forming lipids.

In experiments performed in support of the present invention, liposomes containing PEG-DSPE end-functionalized by hydrazide were prepared. The hydrazide group at the end of a PEG chain can be used for the introduction of other functional groups, or can be used in numerous types of conjugation schemes (Inman). Particularly useful is hydrazide's reactivity toward various glycoproteins, such as immunoglobulins (Wilchek), for attaching these molecules to liposomes.

Gallium 67-labelled, hydrazide end-functionalized PEG liposomes were injected in rats by tail vein injection at about 10–20 micromolar phospholipid/kg body weight. Blood sample were obtained by retroobital bleeding at defined times. The percent of gallium labelled liposomes remaining in the bloodstream was determined at 0, 15 minutes, 1, 3, 5, and 24 hours and is presented in Table 3. The percent injected gallium 67-labelled liposome dose remaining in the blood stream at different times is illustrated in a half log plot versus time in FIG. 10. After 24 hours the animals were sacrificed and tissues removed for label quantitation. The percent of the injected dose found in selected tissues at 24 hours is presented in Table 3.

The blood and tissue retention of Ga-labelled, hydrazide end-functionalized liposomes having two different lipid compositions were also compared in Table 3. A fluid liposome composition was prepared from partially hydrogenated egg phosphatidylcholine (HPEPC). A typical liposome composition contains the hydrazide PEG-DSPE lipid, partially hydrogenated egg PC (PHEPC), and cholesterol in a lipid:lipid:lipid mole ratio of about 0.15:1.85:1. A rigid liposome composition was prepared by substituting hydrogenated serum phosphatidylcholine (HSPC) for PHEPC at the same mole ratio.

As is indicated in Table 3, the fluidity of the liposome composition does not affect the blood retention time of the liposomes. However, the fluidity of the liposome composition does appear to affect the tissue distribution of the end-functionalized liposome. For example, rigid liposomes are preferentially retained by live, spleen and bone tissue. Fluid liposomes are preferentially retained by the kidneys, heart, skin and muscle tissue.

TABLE 3

| % Injected 67 GA Dose Detected at Specified Timepoints | | |
|---|---|---|
| | Peg-HZ Rigid | PEG-Hz Fluid |
| Blood | | |
| 0 | 101.1 ± 12.0 | 100.2 ± 5.4 |
| 15 min. | 89.6 ± 11.2 | 81.6 ± 2.5 |
| 1 hr. | 84 ± 11.1 | 81.7 ± 7.4 |
| 3 hr. | 76 ± 10.5 | 75.3 ± 5.1 |
| 5 hr. | 71.7 ± 10.7 | 66.3 ± 3.8 |
| 24 hr. | 33.4 ± 6.8 | 34.3 ± 0.68 |
| Tissues at 24 hr. | | |
| liver | 12.1 ± 1.2 | 8.8 ± 0.81 |
| spleen | 5.1 ± 0.47 | 4.7 ± 0.64 |
| kidneys | 1.4 ± 0.22 | 1.7 ± 0.25 |
| heart | 0.36 ± 0.037 | 0.77 ± 0.21 |
| lungs | .62 ± 0.23 | 0.58 ± 0.03 |
| skin | .086 ± 0.03 | 0.16 ± 0.08 |

TABLE 3-continued

| % Injected 67 GA Dose Detected at Specified Timepoints | | |
|---|---|---|
| | Peg-HZ Rigid | PEG-Hz Fluid |
| muscle | .08 ± 0.03 | 0.29 ± 0.02 |
| bone | .28 ± 0.09 | 0.04 ± 0.01 |

IV. Therapeutic Effector Compositions

Below are described specific embodiments of the effector composition of the invention, and their intended use as injectable therapeutic agents.

A. Compositions for Enhancing an Immune Response

In one general embodiment, the effector in the liposome composition is a molecule capable of enhancing an immune response when administered parenterally.

1. $F_{ab}$ Effector. The $F_{ab}$ effector composition is used as a passive vaccine to provide humoral immunity against one of a variety of selected pathogenic antigens. The composition is administered to supplement a weakened immune response to a given antigen.

The vaccine effector composition is administered intravenously shortly after exposure to, or shortly before expected exposure to a selected pathogen. The composition is preferably injected in an amount corresponding to between about 0.1 to 2 mg antibody/kg body weight. After IV administration, the composition circulates in the bloodstream, at an effective concentration, for 1–2 days.

2. CD4 Glycoprotein Effector. Numerous therapies for the prevention and treatment of human immunodeficiency virus (HIV) infection and acquired immune deficiency syndrome (AIDS) have been proposed. These therapies target different steps in the process of viral infection. Frequently, therapy includes the administration of drugs which interfere with viral replication, such as AZT and DDI. The adminstration of these drugs is accompanied by toxic side effects, since the replication process of normal cells is also affected.

Another step in the process of viral infection which is targeted in therapy is viral attachment to cells. HIV binds with specificity to the CD4 receptor of CD4+ T cells. By mechanisms not yet fully understood, the CD4+ cells eventually can become infected by HIV. Soluble CD4 receptor polypeptides have been administered intravenously to HIV-infected patients to prevent further HIV infection of a patient's CD4+ T cell population. Heretofore, this therapy has not been effective, since CD4 receptor fragments are rapidly cleared from circulation in the blood stream, and inhibitory plasma concentrations cannot be maintained (Capon). The effector molecule in this embodiment is a soluble CD4 receptor polypeptide capable of binding to the gp120 glycoprotein of human immunodeficiency virus (HIV) to prevent binding of HIV to CD4+ T cells. In a preferred embodiment covalent attachment of CD4 is accomplished by coupling periodate oxidized CD4 with hydrazide group containing liposomes.

CD4 administered as a long-circulating liposomal composition will remain in the blood stream for a longer period of time. The CD4 effector composition can be administered intravenously during early or late stages of HIV infection, most beneficially in combination with other drugs used in AIDS therapeutics, so that HIV particles bound to the liposomes, to the extent these are taken up by infectable cells, will also deliver a dose of the anti-viral agent to the infected cells. AZT and DDI are examples of anti-HIV drugsd which may be encapsulated in the liposome compositions.

The liposome composition should be administered intravenously in a dose equivalent to an effective blood stream CD4 concentration of 1–10 micromolar. Doses of 5–40 mg CD4/kg body weight can be administered, typically at intervals of 2–14 days between treatments, with the level of HIV present in the bloodstream being monitored during treatment by standard assay methods.

Principal advantages of this composition are the increased circulation time of the CD4 effector in the blood stream and the polyvalent presentation of the effector on the surface of the liposomes. Improved affinities of polyvalent CD4 presentation has recently been described (Chen). As described above, CD4 receptor fragments are cleared rapidly by renal filtration. Covalent attachment of the CD4 polypeptide to liposomal carriers prevents renal clearance, and permits circulation of the polypeptide effector composition for 24–48 hours in the blood stream. Additionally, the polyvalent CD4-bearing liposomes resemble CD4+T cell lymphocytes in that the CD4 glycoproteins are presented on hydrophobic surfaces which mimic the surfaces of T cell lymphocytes. This presentation is likely to serve as a decoy binding HIV particles and HIV infected cells expressing gp120 so that healthy CD4+ lymphocytes are spared.

3. Effector for stimulating inflammatory immune responses. Some medical conditions are treated indirectly, by stimulation of the body's natural immune response. Such conditions can include immunodeficiency diseases, such as AIDS, chronic infectious, and certain types of cancers. One immunstimulant therapy involves intravenous injection of cytokines, which can acts to stimulate B cell and T cell immune responses in a variety of ways.

The cytokine effector composition may be administered on a short term basis to enhance a weak immunogenic or weak microbicidal response. Alternatively, the cytokine effector composition may also be administered on a long term basis as part of a therapy treatment for cancer or AIDS. The effector composition may be administered intravenously at doses of about 0.5 to 5.0 mg/kg body weight to enhance an immunogenic response. These doses result in an effective cytokine concentration of about 0.1–1 micromolar in the blood stream.

B. Compositions for Blocking Binding to Cell Receptors

In another general embodiment, the effector in the liposome composition is a molecule capable of blocking the binding of an endogenous agent to a cell receptor, to achieve a desired therapeutic effect.

1. ELAM-1 Binding Inhibitor. As one example, inflammation causes the expression of a polypeptide, endothelial leukocyte adhesion molecule-1 (ELAM-1), on the surface of endothelial cells of the blood vessels. ELAM-1, in turn, recognizes and binds a polysaccharide moiety on surfaces of neutrophils, and recruits neutrophils to sites of inflammation. By preventing the recognition and binding of neutrophils by ELAM-1, excessive inflammatory responses due to conditions, such as reperfusion injury, septic shock, and chronic inflammatory diseases, can be avoided.

In this embodiment, the effector is used to prevent the excessive recruitment of neutrophils to sites of inflammation in the blood stream. The effector is sialyl Lewis$^x$ recognized by ELAM-1 (Phillips). This polysaccharide effector is covalently attached to long-circulating liposomal compositions by the methods described above. In a preferred embodiment attachment of sialyl Lewis$^x$ to liposomes is accomplished via the reducing end of the glucosamine residue. The reducing end can easily react with a hydrazide group of a DSPE-PEG preparation. Coupling of the polysaccharide to the liposomal carrier composition prevents the polysaccharide's clearance by the kidney, and maintains an effective concentration of the polysaccharide effector over a 48 hour period. The liposomal carrier composition is administered in doses of 10 to 50 micrograms/kg body weight in a timely fashion, intravenously, and close to the site of inflammation.

2. Inhibitor of IL-1 Activity. As a second example, the effector is IL-1 inhibitor, which inhibits IL-1's immunostimulatory activity, or IL-1 receptor antagonist (IL1RA), which blocks the binding of IL-1 to lymphocyte cell surfaces. These molecules may be administered to a subject for treatment of septic shock, toxic shock, colonic inflammation, or leukemic cell proliferation. In this aspect of the invention, the liposomal carrier composition is administered in doses of 20 to 50 micrograms/kg body weight on a short term basis for the treatment sepsis, toxic shock or colonic inflammation. The liposomal carrier composition may also be administered at 1 to 2 day intervals on a long term basis for the treatment of leukemia.

Other molecules effective to block the binding of specific cytokines to specific lymphocyte populations may also be employed.

The use of the long-circulating effector composition, for use in blocking the binding of endogenous agents to cell receptor sites, provides two advantages over the use of free effector. First, the effector is maintained in the bloodstream over an extended period, by virtue of blocking renal clearance of the effector. Secondly, the effector molecule, in liposome-bound form, provides greater steric hindrance at the cell surface site of the receptor. Also, the competitive binding or blocking effector and endogenous agent on the receptor site is shifted toward the blocking agent, since the liposomal structure will be displaced at a slower rate kinetically, due to its larger size and number of blocking molecules in the region of the receptor site.

3. Peptide Hormones. In this embodiment the effector composition is useful in the treatment of various diseases that respond to peptide hormones. In one embodiment, the effector is parathyroid hormone (PTH) which is effective to inhibit uncontrolled osteoblast division.

C. Antimicrobial Composition

In this embodiment the effector is a compound which is useful in the prevention and treatment of septic shock. The causal agents of septic shock are endotoxins which accumulate during systemic gram-negative bacterial infections (Jawetz). Because of the rapid onset of severe sepsis, treatment is often not begun until critical stages of sepsis.

The antimicrobial agent which has been used most successfully in treating septic shock against in cases of septic shock is polymyxin B. Because the compound is rapidly excreted, high doses of polymyxin B are required for effective treatment. The high doses, unfortunately, can lead to severe renal toxicity.

In the present invention, polymyxin B circulation in the bloodstream is extended severalfold by its attachment to long-circulating liposomes. The compound is attached to long-circulating liposomal composition carriers by the coupling methods described above.

The liposomal composition is administered on a short term basis, at a dose of 0.1–0.5 mg/kg body weight, as a prophylactic for individuals at risk of, or suffering from acute septic shock. Features of the polymyxin B liposomal composition, already discussed, will minimize polymyxin B's renal accumulation and renal toxicity.

The following examples illustrate methods for preparing derivatized lipids and protein-coated liposomes in accordance with the invention.

EXAMPLE 1

Preparation of DSPE-PEG-Maleimide

A. Preparation of the Mono 2-nitrobenzenesulfonamide of PEG bis(amine) (Compound II).

A mixture of 1.7 g (0.5 mmole) of commercially available polyethylene glycol bis(amine) and 104 mg (0.55 mmole) of 2-nitrobenzene sulfonyl chloride were added to a round-bottomed flask. The minimum amount of dioxane to effect solution (about 15 ml) and 280 microliters of triethylamine (2 mmole) were added. The reaction flask was stoppered and let to stand at room temperature for 4 days.

Thin layer chromatography (TLC) on silica coated plates using a solvent mixture of the following composition $CHCl_3/CH_3OH/H_2O/NH_4OH$; 130/70/8/0.5; v/v/v/v showed fluorescence quenching spots at $R_f=0.87$ to 0.95 and $R_f=0.68$–0.75. The 2-nitro benzene sulfonyl chloride was a more compact spot at $R_f 0.85$. The UV absorbing material at $R_f=0.87$–0.95 probably represented the bis-2-nitrobenzenesulfenamide. The material at $R_f 0.68$–0.75 probably represented the desired mono-2-nitrobenzenesulfonaimde of the starting diamine.

The solvent was evaporated under vacuum to obtain 2.135 g of a yellow syrup. It was dissolved in 5 ml chloroform and placed at the top of a 21 mm×270 mm column of $SiO2$ wetted with chloroform. The product was purified by passing through the column, in sequence:

| 100 ml | 100% chloroform | 0% (1% conc. NH$_4$OH in MeOH) |
|---|---|---|
| 200 ml | 90% " | 10% " |
| 100 ml | 80% " | 20% " |
| 100 ml | 70% " | 30% " |

Fifty ml aliquots were collected separately and assayed by TLC as described above. Most of the yellow, ninhydrin positive-reacting material was eluted in the 20% (1% conc. NH$_4$OH in MeOH) fraction. The fractions were dried and resulted in 397 mg of a bright yellow solid. The yield of the pure sample was about 20%.

B. Preparation of the Imidazole Carbamate of the Mono 2-nitrobenzenesulfonamide of PEG bis(amine) (Compound III).

550 mg (0.15 mmole) of the 2-nitrobenzenesulfonamide of PEG bis(amine) were dissolved in anhydrous benzene. To this was added 49 mg of carbonyl diimidazole (0.3 mmole) and 28 microliters (0.20 mmole) of triethylamine. The air in the reaction vessel was displaced with nitrogen, the flask stoppered and heated in an 80 degree oil bath for 4 hours. TLC on silica-coated plates using the same solvent system as described above, showed that all the starting sulfonamide ($R_f=0.72$) had been consumed, and had been replaced by an iodine absorbing material at $R_f=0.92$. The solvent was removed under vacuum. The residue was dissolved in about 2.5 ml chloroform and transferred to the top of a 21×280 mm cloumn of silica which was wetted with chloroform. The following solvents were passed through the column, in sequence:

| 100 ml | 100% chloroform | 0% (1% conc. NH$_4$OH in MeOH) |
|---|---|---|
| 100 ml | 90% " | 10% " |
| 200 ml | 80% " | 20% " |

50 ml fractions were collected and assayed by TLC, the desired product was found predominantly in the 20% (1% conc. NH$_4$OH in MeOH fraction). When the pooled fractions were evaporated to dryness, 475 mg of a lemon-yellow solid were obtained. This was dissolved in 4.75 ml benzene.

C. Preparation of the DSPE Carbamide of the 2-nitrobenzene Sulfonamide of PEG bis(amine).

To the 450 mg (0.125 mmole) of 2-nitrobenzenesulfonamide of the imidazole carbamide of the PEG bis(amine) dissolved in 4.5 ml benzene was added 93 mg DSPE (0.125 mmole) and 70 microliters (0.50 mmole) of triethylamine. The air was displaced with nitrogen, the flask stoppered and heated in an oil bath at 80 degrees for 6 hours. The flask was cooled to room temperature. DSPE migrates in the above described TLC system with an Rf of 0.54. TLC indicated that all the DSPE had been consumed. The solvent was evaporated under vacuum. The residue was dissolved in 2.5 ml chloroform and placed at the top of a 21×260 mm column of silica wetted with chloroform. The sample was purified by passing through the column in sequence:

| 100 ml | 100% chloroform | 0% (1% conc. NH$_4$OH in MeOH) |
|---|---|---|
| 200 ml | 90% " | 10% " |
| 100 ml | 80% " | 20% " |
| 100 ml | 70% " | 30% " |

The desired product eluted at 20% (1% conc. NH$_4$OH in MeOH), was evaporated and afforded 358 mg of a bright yellow solid with an $R_f=0.95$. Fractions containing imidazole were not used and the final yield of the product (0.0837 mmoles) was 65%.

D. Preparation of the DSPE Carbamide of PEG bis(amine) (Compound IV).

About 358 mg of nitrobenzenesulfenamide of the DSPE carbamate of polyethyleneglycol bis (amine) were dissolved in 10 ml ethanol. To the solution were added 2.4 ml water and 1.2 ml acetic acid. The mixture was allowed to stand at room temperature for 18 hours. TLC analysis showed only partial deprotection. Another 2.3 ml water, and another 1.2 ml acetic acid were added and the reaction was left standing overnight. On silicate coated plates, using a similar solvent system as described above as the developer, flourescence quenching material appeared at $R_f 0.86$ and $R_f 0.74$. The desired ninhydrin reactive, phosphate containing material migrated with an Rf value of 0.637. This spot showed no fluorescence quenching.

The solvent was removed under vacuum. The residue was redissolved in 15 ml chloroform and extracted with 15 ml 5% sodium carbonate. The mixture was centrifuged to effect separation, and the sodium carbonate phase was reextracted 2× with 15 ml chloroform. The combined chloroform extracts were evaporated under reduced pressure to obtain 386 mg of wax. TLC indicated that the wax was largely a ninhydrin positive, phosphate containing lipid of $R_f 0.72$.

The wax was dissolved in 2.5 ml chloroform and placed on a silicate column which had been wetted with chloroform. The following solvents were passed through the column in sequence:

| 100 ml | of | 100% chloroform | 0% (1% CONC. NH$_4$OH in MeOH) |
|---|---|---|---|
| 100 ml | | 90% | 10% |
| 100 ml | | 80% | 20% |
| 100 ml | | 70% | 30% |
| 100 ml | | 50% | 50% |
| 100 ml | | 0% | 100% |

The samples were assayed by TLC. The desired product was found in the factions with 30% and 50% (1% conc. NH$_4$OH in methanol). These samples were combined and evaporated to dryness under vacuum to afford 91 mg (22 micromoles) of a viscous syrup.

E. Preparation of the Maleic Acid Derivative of the DSPE Carbamide of PEG bis(amine) (Compound V).

To 18 micromoles of the DSPE carbamide of PEG bis (amine) described above, dissolved in 1.8 ml chloroform, was added 3.5 mg (36 micromoles) maleic anhydride and 5 microliters (36 micromoles) triethylamine. The stoppered flask was allowed to stand at room temperature for 24 hours. The solvent was evaporated. TLC on silica plates indicated that all the starting material, had been replaced by a ninhydrin negative, phosphate containing material of Rf=0.79–1.00.

F. Preparation of the Maleimide of the DSPE Carbamide of PEG bis (amine) (Compound VI).

The syrup was dissolved in 2 mls acetic anhydride saturated with anhydrous sodium acetate. The solution was heated in a 50 degree Centigrade oil bath for two hours. 10 ml ethanol were added and evaporated under vacuum. This step was repeated twice to remove excess acetic anhydride and acetic acid. The residue was taken up 1 ml chloroform, and passed through a silica column with the following solvents in sequence:

| 100 ml | 100% chloroform | 0% (1% cono. NH$_4$OH in MeOH) |
|---|---|---|
| 200 ml | 90% " | 10% " |
| 100 ml | 80% " | 20% " |
| 100 ml | 70% " | 30% " |

50 ml samples were collected, and the main product was found in the fractions eluted with 10% of 1% conc. NH$_4$OH in MeOH. The fractions were combined and then evaporated to dryness under vacuum which afforded 52 mg of a pale, yellow, viscous oil, which by TLC migrated with an Rf of 0.98 and contained phosphate. 12.3 micromoles product were obtained which corresponded to a yield of about 34%.

EXAMPLE 2

Preparation DSPE-PEG 3-(2-pyridyldithio) Propionamide

The DSPE carbamide of PEG bis (amine) (50 micromoles) is dissolved in 3 ml of anhydrous methanol containing 50 micromoles of triethylamine and 25 mg of N-succinimidyl 3-(2-pyridyldithio) propionate (SPDP). The reaction is carried out at room temperature for 5 hours under an argon atmosphere. Methanol is removed under reduced pressure, and the products were redissolved in chloroform and applied to a 10 ml silica gel column which had been activated at 150 degrees overnight and had been prewashed. A similar solvent system as used in Example 1 is used to purify the product. Analysis on TLC plates indicates a product with an R$_f$=0.98 which reacts negatively with ninhydrin, contains phosphate and has no free sulfhydryl groups. When the product is treated with excess dithiothreitol, 2-thiopyridinone is released.

EXAMPLE 3

Preparation of the Aldehyde of the Ethylene-Linked PEG-DSPE

A. Preparation of I-trimethylsilyloxy-PEG (Compound X)

15.0 gm (10 mmoles) of PEG) N.Wt. 1500, (Aldrich Chemical) was dissolved in 80 ml benzene. 1.40 ml (11 mmoles) of chlorotrimethyl silane (Aldrich Chemical Co.) and 1.53 ml (1 mmoles) of triethylamine was added. The mixture was stirred at room temperature under an inert atmosphere for 5 hours.

The mixture was filtered by suction to separate crystals of triethylammonium chloride and the crystals were washed with 5 ml benzene. Filtrate and benzene wash liquids were combined. This solution was evaporated to dryness under vacuum to provide 15.83 grams of colorless oil which solidified on standing.

TLC of the product on Si—C$_{18}$ reversed-phase plates using a mixture of 4 volumes of ethanol with 1 volume of water as developer, and iodine vapor visualization, revealed that all the polyglycol 1500 (R$_f$>0.93) has been consumed, and was replaced by a material of R$_f$=0.82. An infra-red spectrum revealed absorption peaks characteristic only of polyglycols.

Yield of I-trimethylsilyoxyPEG, M.W. 1500 was nearly quantitative.

B. Preparation of Trifluoromethane Sulfonyl Ester of trimethylsilyloxy-PEG (Compound XI)

15.74 grams (10 mmol) of the crystalline I-trimethylsilyloxy PEG obtained above was dissolved in 40 ml anhydrous benzene and cooled in a bath of crushed ice. 1.53 ml (11 mmol) triethylamine and 1.85 ml (11 mmol) of trifluoromethanesulfonic anhydride obtained from Aldrich Chemical Co. were added and the mixture was stirred over night under an inert atmosphere until the reaction mixture changed to a brown color.

The solvent was then evaporated under reduced pressure and the residual syrupy paste was diluted to 100.0 ml with methylene chloride. Because of the great reactivity of trifluoromethane sulfonic esters, no further purification of the trifluoromethane sulfonyl ester of I-trimethylsilyloxy PEG was done.

C. Preparation of N-1-trimethylsilyloxy PEG 1500 PE (Compound XII).

10 ml of the methylene chloride stock solution of the trifluoromethane sulfonyl ester of 1-trimethylsilyloxy PEG was evaporated to dryness under vacuum to obtain about 1.2 grams of residue (approximately 0.7 mmoles). To this residue, 3.72 ml of a chloroform solution containing 372 mg (0.5 mmoles) egg PE was added. To the resulting solution, 139 microliters (1.0 mmole) of triethylamine was added and the solvent was evaporated under vacuum. To the obtained residue, 5 ml dry dimethyl formamide and 70 microliters (0.50 mmoles) triethylamine (VI) was added. Air from the reaction vessel was displaced with nitrogen. The vessel was closed and heated in a sand bath a 110° C. for 22 hours. The solvent was evaporated under vacuum to obtain 1.58 grams of brownish colored oil.

A 21×260 mm chromatographic absorption column filled with Kieselgel 60 silica 70–230 mesh, was prepared and rinsed with a solvent composed of 40 volumes of butanone, 25 volumes acetic acid and 5 volumes of water. The crude product was dissolved in 3 ml of the same solvent and transferred to the top of the chromatography column. The chromatogram was developed with the same solvent and sequential 30 ml portions of effluent were assayed each by TLC.

The TLC assay system used silica gel coated glass plates, with solvent combination butanone/acetic acid/water; 40/25/5; v/v/v. Iodine vapor absorption served for visualization. In this solvent system, the N-1-trimethylsilyoxy PEG 1500 PE appeared at $R_f$=0.78. Unchanged PE appeared at $R_f$=0.68.

The desired N-1-trimethylsilyloxy PEG 1500 PE was a chief constituent of the 170–300 ml portions of column effluent. When evaporated to dryness under vacuum these portions afforded 111 mg of pale yellow oil of product.

D. Preparation of N-polyethylene glycyl 1500: PE (Compound XII).

Once-chromatographed, PE compound was dissolved in 2 ml of tetrahydrofuran. To this, 6 ml acetic acid and 2 ml water was added. The resulting solution was let to stand for 3 days at 23° C. The solvent from the reaction mixture was evaporated under vacuum and dried to constant weight to obtain 75 mg of pale yellow wax. TLC on Si—C18 reversed-phase plates, developed with a mixture of 4 volumes ethanol, 1 volume water, indicated that some free PE and some polyglycol-like material formed during the hydrolysis.

The residue was dissolved in 0.5 ml tetrahydrofuran and diluted with 3 ml of a solution of ethanol water; 80:20; v:v. The mixture was applied to the top of a 10 mm×250 mm chromatographic absorption column packed with octadecyl bonded phase silica gel and column was developed with ethanol water 80:20% by volume, collecting sequential 20 ml portions of effluent. The effluent was assayed by reversed phase TLC. Fractions containing only product of Rf=0.08 to 0.15 were combined. This was typically the 20–100 ml portion of effluent. When evaporated to dryness, under vacuum, these portions afforded 33 mg of colorless wax PEG-PE corresponding to a yield of only 3%, based on the starting phosphatidyl ethanolamine.

NMR analysis indicated that the product incorporated both PE residues and PEG residues. The product prepared was used for a preparation of PEG-PE liposomes.

E. Preparation of the Aldehyde of PEG-DSPE (Compound XIII).

The free hydroxyl group on PEG derivatized by DSPE can be oxidized to the corresponding aldehyde in the following manner prior to incorporation of the linear polymers into liposomes (Harris). About 2.7 g PEG1500-DSPE (1 mmole), which is prepared as in Example 3, is added to 0.4 g acetic anhydride in 15 ml dimethylsulfoxide with stirring for 30 hours at room temperature. At this point the reaction mixture is neutralized with dilute sodium hydroxide, the solvent is evaporated under reduced pressure.

The residue is dissolved in 10 ml chloroform, washed with two successive 10 ml portions of water, and centrifuged to separate chloroform and water phases. The chloroform phase is evaporated under vacuum to obtain a wax. The wax is re-dissolved in 5 ml chloroform and transferred to the top of a 21×270 mm column of silica gel moistened with chloroform. The column is developed by passing 100 ml of solvent through the column. The following solvents were used in sequence:

| Volume % Chloroform | Volume % Methanol Containing 2% Conc. Ammonium Hydroxide/methanol |
|---|---|
| 100% | 0% |
| 95% | 5% |
| 90% | 10% |
| 85% | 15% |
| 80% | 20% |
| 70% | 30% |
| 60% | 40% |
| 50% | 50% |
| 0% | 100% |

Separated 50 ml fractions of column effluent are saved. The fractions of the column are separated by TLC on Si—C18 reversed-phase plates. TLC plates are developed with 4 volumes of ethanol mixed with 1 volume of water. Visualization is done by exposure to iodine vapor.

Only those fractions containing an iodine-absorbing lipid of $R_f$ about 0.20 were combined and evaporated to dryness under vacuum and dried in high vacuum to constant weight. In this way 94 mg of waxy crystalline solid was obtained of M.W. 2226. The conversion of the terminal alcohol to the aldehyde can be monitored by IR.

EXAMPLE 4

Synthesis of N-hydroxysuccinimide Ester of α-hydroxy-Ω-(carboxymethylamino-carbonyl) oxy-poly(oxylene) (Compound XXIV) and Coupling to DSPE α-hydroxy-Ω-carboxy derivative of PEG (XXIX) (2 g, ≈1 mmol) and N-hydroxysuccinimide (0.23 g, 2 mmol) were dissolved in methylene chloride-ethyl acetate (4 ml, 1:1). The solution was cooled on ice-water bath and treated with dicyclohexylcatbodiimide (DCC) (0.25 g, 1.2 mmol) pre-dissolved in ethyl acetate (1 ml). Within a few minutes the solution became cloudy as dicyclohexylurea (DCU) appeared. After 2 hours the reaction mixture was filtered from DCU and evaporated into dryness. The polymer was crystallized from isopropanol and dried in vacuo over $P_2O_5$. Yield: 1.5 g (70%). Titration of the product for active acyl content (Zalipsky, 1991) gave $4.8·10^{-5}$ mole/g (104% of the theoretical value). H-NMR (CDCl$_3$) spectra showed in addition to characteristic singlets of PEG (δ=3.64) and N-hydroxysuccinimide (δ=2.84) also triplet of CH$_2$—(C=0)—Gly (δ=4.27) and doublet of methylene group of Glycine residue (δ=4.33) some isopropanol was also present (δn=1.20, 3, J=6 Hz).

N-hydroxysuccinimide ester of α-hydroxy-ω-carboxy-PEG (0.52 g, 0.2 mmol) was added to DSPE (0.14 g, 0.185 mmol) suspension in chloroform (2 ml) followed by triethylamine (0.1 ml, 0.86 mmol). After mixing the mixture was heated on water bath at 55° C. for 5 minutes. During this time the solution became clear. TLC (chloroform-methanol-water 90:18:2) on silica gel G showed complete conversion of DSPE into a new product, which gave no color with ninhydrin yet like excess of PEG was readily visualized by iodine vapor. The solution was treated with an equivalent amount of acetic acid to neutralize the TEA and evaporated into dryness. The residue was dissolved in water and extensively dialyzed through 300,000 MWCO cellulose acetate membrane at 4° C., filtered through 0.2 μm and lyophilized, yielding pure compound XXIV (360 mg, ≈70%).

EXAMPLE 5

Preparation of DSPE-PEG-Hydrazide (Compound XXXII)

A. Preparation of ω-Hydroxy Acid Derivative of PEG, α-(Hydroxyethyl)-ω-(carboxymethylaminocarbonyl) oxy-poly(oxyethylene)(Compounds XIX and XXIX).

Polyethylene glycol (Fluka, PEG-2000, 42 g, 42 mequiv OH) is dissolved in toluene (200 ml) and azeotropically dried (Zalipsky, 1987), and treated with ethyl isocyanotoacetate (2.3 ml, 21 mmol) and triethylamine (1.5 ml, 10 mmol). After overnight reaction at 25° C. the solution is evaporated to dryness. The residue is dissolved in 0.2 M NaOH (100 ml) and any trace of toluene is evaporated. The solution is maintained at pH 12 with periodical dropwise additions of 4 M NaOH.

When the solution pH is stabilized at pH 12, the solution is acidified to pH 3.0 and the product is extracted with methylene chloride (100 ml×2). TLC on silica gel G (isopropyl alcohol/$H_2O$/conc. ammonia 10:2:1) gives a typical chromatogram of partially carboxylated PEG (Zalipsky, 1990) consisting of unreacted PEG ($R_f$=0.67), monocarboxylated derivative ($R_f$=0.55) and dicarboxylated derivative of the polymer ($R_f$=0.47). This solution is dried over ($MgSO_4$), filtered and evaporated to dryness. The PEG mixture is dissolved in water (50 ml). One-third of this solution (30 ml ≈14 g of derivatized PEG) is loaded onto DEAE-Sephadex A-25 (115 ml of gel in borate form). After the underivatized PEG is washed off the column with water (confirmed by negative polymethacylic acid (PMA) test, (Zalipsky, 1990) gradient of ammonium bicarbonate (2–20 mM at increments of 1–2 mM every 200 ml) was applied, and 50 ml fractions collected. Fractions 1–25 contain only PEG monoacid as determined by PMA and TLC tests. These fractions are pooled together, concentrated to ≈70 ml, acidified to pH 2 and extracted with methylene chloride (50 ml×2). The $CH_2Cl_2$ solution is dried ($MgSO_4$), concentrated and poured into cold stirring ether. The precipitated product is dried in vacuo. Yield: 7 g. Titration of carboxyl groups gives $4.6·10^{-4}$ mequiv/g (97% of theoretical value).

B. Preparation of Compound XXX. The w-hydroxy acid derivative of PEG (5 g, 2.38 mmol) and tert-butyl carbazate (0.91 g, 6.9 mmol) are dissolved in $CH_2Cl_2$-ethyl acetate (1:1, 7 ml). The solution is cooled on ice and treated with DCC (0.6 g, 2.9 mmol) predissolved in the same solvent mixture. After 30 minutes the ice bath is removed and the reaction is allowed to proceed for an additional 3 hours. The reaction mixture is filtered from dicyclohexylurea and evaporated. The product is recovered and purified by two precipitations from ethyl acetate-ether (1:1) and dried in vacuo over $P_2O_5$. Yield: 5.2 g, 98%. TLC of the product gave one spot ($R_f$=0.68) instead of the starting material ($R_f$=0.55). H-NMR ($CDCl_3$): δ1.46 (s, t-Bu, 9H); 3.64 (s, PEG, 178H); 3.93 (br. d, J=4.5, $CH_2$ of Gly, 2H); 4.24 (t, C$\underline{H}_2$—OCO-Gly, 2H) ppm. $^{13}$C-NMR ($CDCl_3$): δ28.1 (t-Bu); 43.4 ($CH_2$ of Gly); 61.6 ($CH_2OH$); 64.3 ($\underline{C}H_2OCONH$); 69.3 ($\underline{C}H_2CH_2O$ CONH); 70.5 (PEG); 72.4 ($\underline{C}H_2CH_2OH$); 81.0 ($CMo_3$); 155.1 (C=O of Boc); 156.4 (C=O of Gly urethane; 168.7 (C=O of Gly hydrazide) ppm.

C. Preparation of Compound XXXI. The ω-hydroxy Boc-hydrazide derivative of PEG (5 g, 2.26 mmol) is dissolved in pyridine (1.1 ml), $CH_2Cl_2$ (5 ml) and $CH_3CN$ (2 ml) and treated with disuccinimidyl carbonate (1.4 g, 5.5 mmol) at 25° C. overnight. The solution is filtered and gradually added to cold ethyl ether (100 ml). The precipitated product is dissolved in warm ethyl acetate (45 ml), chilled and mixed with equal volume of ethyl ether. The precipitate is collected by filtration and dried in vacuo over $P_2O_5$. Yield: 4.8 g, 90%. succinimidyl carbonate groups content $4.15·10^{-4}$ mequiv/g (98% of theoretical value) was determined by titration (Zalipsky, 1991). H-NMR ($CDCl_3$): δ1.46 (s, t-Bu, 9H); 2.83 (s, succinimide); 3.64 (s, PEG, 178H); 3.79 (t, C$\underline{H}_2OCO_2$-Su); 3.93 (br. d, J=4.5, $CH_2$ of Gly, 2H); 4.24 (t, C$\underline{H}_2$—OCO-Gly, 2H); 4.46 (t, C$\underline{H}_2OCO_2$-Su) ppm.

D. Preparation of Compound XXXII. To prepare the DSPE-PEG-hydrazide a slight excess of succinimidyl carbonate Boc-protected PEG-glycine hydrazide, prepared above, is reacted with DSPE suspended in chloroform in the presence of triethylamine. The lipid derivative is quickly (5–10 minutes) solubilized in the process of this reaction. The excess of heterobifunctional PEG is removed by dialysis using 300,000 MWCO cellulose ester dialysis membrane from Spectrum. The recovered lipid conjugate was subjected to conventional Boc-deprotection conditions (4M HCl in dioxane for 30 minutes) and then further purified by recrystallization. H-NMR ($CDCl_3$): δ0.88 (t, $CH_3$,6H); 1.59 (t, C$\underline{H}_2CH_2CO$, 4H); 2.84 (t, $CH_2CO$, 4H); 3.64 (s, PEG, 180H); 4.0 (t); 4.2 (m, $CH_2OCO-NH_2$); 4.4–4.3 (two doublets); 5.2 (g, CH of glyceride).

EXAMPLE 6

Preparation of Liposomes with Covalently Bound β-Galactosidase

The maleimide of the DSPE carbamide of polyoxyethylene bis (amine) (3500-DSPE) was prepared as in Example 1. β-Galactosidase was purchased from Pierce (Rockford, Ill.). Enzyme assays with o-nitrophenyl galactose were performed essentially by monitoring the development of the colored product with an extinction coefficient of 4467 at 413 nanometers in 0.1 N sodium hydroxide. The assay mixture consisted of 86 mM sodium phosphate pH 7.3, 1 mM magnesium chloride, 50 mM-beta-mercaptoethanol and 2.3 mM o-nitrophenyl galactose and product formation was monitored for 10 to 15 minutes in the linear range of the assay.

Liposomes (MLV's) were prepared according to standard methods and sized with one of the following compositions indicated in Table 4. The liposomes were sized by extrusion through a polycarbonate membrane to 200 nm.

TABLE 4

| "Phenotype" | | | | | Mol % | | |
|---|---|---|---|---|---|---|---|
| PEG-DSPE | Crosslinker | αT | Ch | Pc | Cross-linker | PEG-DSPE | PG |
| − | − | 1 | 33 | 61 | — | — | 5 |
| + | − | 1 | 33 | 61 | — | 5 | — |
| − | + | 1 | 33 | 56 | 5 | — | 5 |
| + | + | 1 | 33 | 56 | 5 | 5 | — | where α-T=α-tocopherol (antioxidant), Ch=cholesterol, PC=partially hydrogenated egg PC (IV 40), crosslinker=the maleimide derivative of PEG3500-DSPE, and PG=egg phosphatidyl glycerol. In addition all liposome preparations were "spiked" with a $^3$H-DPPC tracer. The total lipid concentration in each preparation, after hydration in PBS (50 mM sodium phosphate pH 7.2, 50 mM sodium chloride, was 2 mM.

Crosslinking reactions were performed by adding enzyme solution to the liposomes (final protein concentration=0.5 mg/ml) and incubating the suspension overnight at ambient temperature with gentle shaking. Unreacted crosslinker was then quenched with 10 mM 2-mercaptoethanol (2-ME) for 30–60 minutes at 37° C. Liposomes were separated from unconjugated protein by flotation through a metrizamide gradient: the sample was brought to 30% (w/v) metrizamide and transferred to an SW60Ti tube, 20% metrizamide was layered above, then PBS was added on top to provide an aqueous interface. Gradients were centrifuged at 45,000 rpm for 60 minutes at 40° C., then each liposomal band, easily visible at the PBS interface, was collected and transferred to dialysis tubing. Dialysis proceeded overnight at 4° C. against two changes of PBS. Removal of the metrizamide was necessary because it inhibits β-galactosidase activity significantly even at 1% (w/v) concentration.

EXAMPLE 6

Liposome Blood Lifetime Measurements of Hydrazide End-Functionalized PEG Liposomes A. Preparation of Hydrazide End-Functionalized Liposomes Hydrazide PEG-DSPE composed of PEG, end-functionalized with a hydrazide group, and distearyl-PE was prepared as described. The hydrazide PEG-DSPE lipid was combined with partially hydrogenated egg PC (PHEPC) and cholesterol in a lipid:lipid:lipid mole ratio of about 0.15:1.85:1 and the lipid mixture was hydrated. Generally, lipid hydration occured in the presence of desferal mesylate, followed by sizing to 0.1 micron, and removal of non-entrapped desferal by gel filtration with subsequent loading of Ga-oxide into the liposomes. The unencapsulated Ga was removed during passage through a Sephadex G-50 gel exclusion column. Both compositions contained 10 micromoles/ml in 0.15 M NaCl, 5 mM desferal.

A second lipid mixture was prepared in a similar manner but with HSPC instead of PHEPC.

B. Measuring Blood Circulation Time and Tissue Levels.

In vivo studies of liposomes were performed in laboratory rats at 200–300 g each. These studies involved tail vein injection of liposome samples at about 10–20 micromolar phospholipid/kg body weight. Blood sample were obtained by retroobital bleeding at defined times. The animals were sacrificed after 24 hours and tissues removed for label quantitation. The weight and percent of the injected dose in each tissue was determined. The studies were carried out using $^{67}$Ga-desferal loaded liposomes and radioactivity was measured using a gamma counter. The percent of the injected dose remaining in the blood at several time points up to 24 hours, and in selected tissues at 24 hours was determined.

1. Plasma Kinetics of Hydrazide-PEG Liposomes.

The liposome composition (0.4 ml) was injected IV in animals. At times 0, 0.25, 1, 3, or 5 and 24 hours after injection, blood samples were removed and assayed for the amount of Ga-desferal remaining in the blood, expressed as a percentage of the amount measured immediately after injection. Hydrazide-PEG liposome have a blood halflife of about 15 hours, and nearly 30% of the injected material is present in the blood after 24 hours.

2. 24 Hour Tissue Levels.

Studies to determine the distribution of gallium labelled liposomes in selected tissues, 24 hours after intravenous liposome injection, were carried out. The liposome composition (0.4 ml) was injected IV in animals. The percent dose remaining in tissues 24 hours after intravenous administration are shown in Table 3.

While the invention has been described with reference to specific methods and embodiments, it will be appreciated that various modifications and changes may be made without departing from the invention.

It is claimed:

1. A liposome composition, comprising
   liposomes, each having an outer layer of hydrophilic chains, and
   an effector molecule attached to the distal ends of said chains
   wherein binding of the liposomes to a first binding member or a second binding member is effective to inhibit binding between said first and second binding members.

2. The composition of claim 1 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

3. The composition of claim 2 wherein the polysaccharide is sialyl Lewis$^x$.

4. The composition of claim 2 wherein the cytokine is selected from the group consisting of interferons, interleukins, TNF, transforming growth factor β, lymphotoxin, GM-CSF, and G-CSF.

5. The composition of claim 4 wherein the interferon is selected from the group consisting of IFN-alpha, IFN-beta, and IFN-gamma.

6. The composition of claim 4 wherein the interleukin is selected from the group consisting of IL-1α, IL-1β, IL-2, IL-3, IL-4, IL-5, IL-6, IL-7, and IL-8.

7. A liposome composition for use in treating a condition mediated by binding of one binding member to a second binding member, comprising
   liposomes, each having an outer layer of hydrophilic polymer chains, and
   an effector molecule attached to the distal ends of said chains
   wherein binding of the liposomes to one of said first or second binding members is effective to inhibit binding between said first and second binding members.

8. The composition of claim 7 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

9. The composition of claim 8 wherein the polysaccharide is sialyl Lewis$^x$.

10. The composition of claim 8 wherein the cytokine is selected from the group consisting of interferons, interleukins, TNF, transforming growth factor β, lymphotoxin, GM-CSF, and G-CSF.

11. The composition of claim 10 wherein the interferon is selected from the group consisting of IFN-alpha, IFN-beta, and IFN-gamma.

12. The composition of claim 10 wherein the interleukin is selected from the group consisting of IL-1α, IL-1β, IL-2, IL-3, IL-4, IL-5, IL-6, IL-7, and IL-8.

13. A liposome composition for use in treating a condition mediated by binding of one binding member, which is present in the bloodstream, to a second binding member, comprising
    liposomes, each having an outer layer of hydrophilic polymer chains, and
    an effector molecule attached to the distal ends of said chains wherein binding of the liposomes to one of said first or second binding members is effective to inhibit binding between said first and second binding members.

14. The composition of clam 13 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

15. The composition of claim 14 wherein the polysaccharide is sialyl Lewis$^x$.

16. The composition of claim 14 wherein the cytokine is selected from the group consisting of interferons, interleukins, TNF, transforming growth factor β, lymphotoxin, GM-CSF, and G-CSF.

17. The composition of claim 16 wherein the interferon is selected from the group consisting of IFN-alpha, IFN-beta, and IFN-gamma.

18. The composition of claim 16 wherein the interleukin is selected from the group consisting of IL-1α, IL-1β, IL-2, IL-3, IL-4, IL-5, IL-6, IL-7, and IL-8.

19. A liposome composition for use in treating a condition mediated by binding of a first binding member, which is a pathogen or cell in the bloodstream, to a second binding member comprising
liposomes, each having an outer layer of hydrophilic polymer chains, and
an effector molecule attached to the distal ends of said chains
wherein binding of the liposomes to one of said first or second binding members is effective to inhibit binding between said first and second binding members.

20. The composition of claim 19 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

21. The composition of claim 20 wherein the polysaccharide is sialyl Lewis$^x$.

22. The composition of claim 20 wherein the cytokine is selected from the group consisting of interferons, interleukins, TNF, transforming growth factor β, lymphotoxin, GM-CSF, and G-CSF.

23. The composition of claim 22 wherein the interferon is selected from the group consisting of IFN-alpha, IFN-beta, and IFN-gamma.

24. The composition of claim 22 wherein the interleukin is selected from the group consisting of IL-1α, IL-1β, IL-2, IL-3, IL-4, IL-5, IL-6, IL-7, and IL-8.

25. A liposome composition for use in treating a condition mediated by binding of a first binding member to a second binding member, which is a target cell, comprising
liposomes, each having an outer layer of hydrophilic polymer chains, and
an effector molecule attached to the distal ends of said chains
wherein binding of the liposomes to one of said first or second binding members is effective to inhibit binding between said first and second binding members.

26. The composition of claim 25 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

27. The composition of claim 26 wherein the polysaccharide is sialyl Lewis$^x$.

28. The composition of claim 26 wherein the cytokine is selected from the group consisting of interferons, interleukins, TNF, transforming growth factor β, lymphotoxin, GM-CSF, and G-CSF.

29. The composition of claim 28 wherein the interferon is selected from the group consisting of IFN-alpha, IFN-beta, and IFN-gamma.

30. The composition of claim 28 wherein the interleukin is selected from the group consisting of IL-1α, IL-1β, IL-2, IL-3, IL-4, IL-5, IL-6, IL-7, and IL-8.

31. A liposome composition for use in treating a condition mediated by binding of a first binding member, which is a pathogen, to a second binding member, which is a target cell, comprising
liposomes, each having an outer layer of hydrophilic polymer chains, and
an effector molecule attached to the distal ends of said chains
wherein binding of the liposomes to one of said first or second binding members is effective to inhibit binding between said first and second binding members.

32. The composition of claim 31 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

33. The composition of claim 32 wherein the polysaccharide is sialyl Lewis$^x$.

34. The composition of claim 32 wherein the cytokine is selected from the group consisting of interferons, interleukins, TNF, transforming growth factor β, lymphotoxin, GM-CSF, and G-CSF.

35. The composition of claim 34 wherein the interferon is selected from the group consisting of IFN-alpha, IFN-beta, and IFN-gamma.

36. The composition of claim 34 wherein the interleukin is selected from the group consisting of IL-1α, IL-1β, IL-2, IL-3, IL-4, IL-5, IL-6, IL-7, and IL-8.

37. A liposome composition for use in treating a condition mediated by binding of a first binding member, which is a cell in the bloodstream, to a second binding member, which is a target cell, comprising
liposomes, each having an outer layer of hydrophilic polymer chains, and
an effector molecule attached to the distal ends of said chains
wherein binding of the liposomes to one of said first or second binding members is effective to inhibit binding between said first and second binding members.

38. The composition of claim 37 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

39. The composition of claim 38 wherein the polysaccharide is sialyl Lewis$^x$.

40. The composition of claim 38 wherein the cytokine is selected from the group consisting of interferons, interleukins, TNF, transforming growth factor β, lymphotoxin, GM-CSF, and G-CSF.

41. The composition of claim 40 wherein the interferon is selected from the group consisting of IFN-alpha, IFN-beta, and IFN-gamma.

42. The composition of claim 40 wherein the interleukin is selected from the group consisting of IL-1α, IL-1β, IL-2, IL-3, IL-4, IL-5, IL-6, IL-7, and IL-8.

43. A liposome composition for use in treating a condition mediated by binding of a first binding member, which is a pathogen or a cell in the bloodstream, to a second binding member, which is a target cell, comprising liposomes, each having an outer layer of hydrophilic polymer chains, and an effector molecule attached to the distal ends of said chains wherein binding of the liposomes to one of said first or second binding members is effective to inhibit binding between said first and second binding members.

44. The composition of claim 43 wherein the effector molecule is selected from the group consisting of $F_{ab}$ antibody fragments, cytokines, cellular growth factors, peptide hormones, monosaccharides, polysaccharides, IL-1 inhibitors, ELAM-1 binding inhibitors, and limulus antilipopolysaccharide factor (LALF).

45. The composition of claim 44 wherein the polysaccharide is sialyl Lewis$^x$.

46. The composition of claim 44 wherein the cytokine is selected from the group consisting of interferons, interleukins, TNF, transforming growth factor β, lymphotoxin, GM-CSF, and G-CSF.

47. The composition of claim 46 wherein the interferon is selected from the group consisting of IFN-alpha, IFN-beta, and IFN-gamma.

48. The composition of claim 46 wherein the interleukin is selected from the group consisting of IL-1α, IL-1β, IL-2, IL-3, IL-4, IL-5, IL-6, IL-7, and IL-8.

* * * * *